US008735156B2

(12) United States Patent
Hamra

(10) Patent No.: US 8,735,156 B2
(45) Date of Patent: May 27, 2014

(54) PRODUCTION AND USE OF RAT SPERMATOGONIAL STEM CELL LINES

(75) Inventor: Franklin Kent Hamra, Keller, TX (US)

(73) Assignee: The Board of Regents of The University of Texas System

( * ) Notice: Subject to any disclaimer, the term of this patent is extended or adjusted under 35 U.S.C. 154(b) by 0 days.

(21) Appl. No.: 13/132,301

(22) PCT Filed: Dec. 1, 2009

(86) PCT No.: PCT/US2009/066275
§ 371 (c)(1),
(2), (4) Date: Jun. 1, 2011

(87) PCT Pub. No.: WO2010/065550
PCT Pub. Date: Jun. 10, 2010

(65) Prior Publication Data
US 2011/0302666 A1 Dec. 8, 2011

Related U.S. Application Data

(60) Provisional application No. 61/187,498, filed on Jun. 16, 2009, provisional application No. 61/119,005, filed on Dec. 1, 2008.

(51) Int. Cl.
*C12N 5/02* (2006.01)
*A01N 1/00* (2006.01)
*C12N 5/10* (2006.01)
*A01N 63/00* (2006.01)

(52) U.S. Cl.
USPC ............ 435/404; 435/1.1; 435/325; 435/353; 435/378; 435/385; 424/93.7

(58) Field of Classification Search
USPC ........... 435/404, 1.1, 325, 378, 385; 424/93.7
See application file for complete search history.

(56) References Cited

U.S. PATENT DOCUMENTS

| 2007/0136830 A1 | 6/2007 | Hammer et al. |
| 2007/0192881 A1 | 8/2007 | Brinster et al. |
| 2008/0066197 A1 | 3/2008 | Ying et al. |
| 2008/0178311 A1 | 7/2008 | Readhead et al. |

FOREIGN PATENT DOCUMENTS

| EP | 1594971 | | 11/2005 |
| EP | 1594972 | | 11/2005 |
| EP | 1594973 | | 11/2005 |
| WO | WO 2004/070042 | * | 8/2004 |
| WO | 2007056551 A2 | | 5/2007 |
| WO | WO 2008098181 | * | 8/2008 |
| WO | 2009071334 A2 | | 6/2009 |

OTHER PUBLICATIONS

Hamra et al., Defining the spermatogonial stem cell Developmental Biology vol. 269, Issue 2, May 15, 2004, pp. 393-410.*

Wu et al., Spermatogonial Culture Medium: An Effective and Efficient Nutrient Mixture for Culturing Rat Spermatogonial Stem Cells, Biology of Reproduction (2009) 81:77-86.
Hamra et al., Defining the Spermatogonial Stem Cell, Developmental Biology (2004) 269:393-410.
Ivics et al., Sleeping Beauty Transposon Mutagenesis of the Rat Genome in Spermatogonial Stem Cells, Methods (2011) 53:356-365.
Keng et al., Region-specific Saturation Germline Mutagenesis in Mice Using the Sleeping Beauty Transposon System, Nature Methods (2005) 2(10):763-769.
Takeda et al., Insertional Mutagenesis of the Mouse Germline with Sleeping Beauty Transposition, Methods in Mol Biol. (2008) 435:109-125.
Brinster et al., "Germline transmission of donor haplotype following spermatogonial transplantation", Proc Natl Acad Sci USA,1994, 91:11303-11307.
Brinster et al., "Spermatogenesis following male germ-cell transplantation", Proc Natl Acad Sci USA, 1994, 91:11298-11302.
Clouthier et al., "Rat spermatogenesis in mouse testis", Nature, 1996, 381:418-421.
Kanatu-Shinohara et al., "Long-term proliferation in culture and germline transmission of mouse male germline stem cells", Biol Reprod, 2003, 69:612-616.
Nagano et al., "Culture of mouse spermatogonial stem cells", Tissue and Cell, 1998, 30:389-397.
Nagano et al., "Pattern and kinetics of mouse donor spermatogonial stem cell colonization in recipient testes", Biol Reprod, 1999, 60:1429-1436.
Mahato et al., "Spermatogenic cells do not require estrogen receptor-alpha for development or function", Endocrinology, 2000, 141:1273-1276.
Mahato et al., "Estrogen receptor-alpha is required by the supporting somatic cells for spermatogenesis", Mol Cell Endocrinol, 2001, 178:57-63.
Ogawa et al., "Transplantation of male germ line stem cells restores fertility in infertile mice", Nat Med, 2000, 6:29-34.
Shinohara et al., "Rats produced by interspecies spermatogonial transplantation in mice and in vitro microinsemination", Proc Natl Acad Sci USA, 2006, 103:13624-13628.
Zhang et al., "The radiation-induced block in spermatogonial differentiation is due to damage to the somatic environment, not the germ cells", J Cell Physiol, 2007, 211:149-158.
Kazuki et al., "Correction of a genetic defect in multipotent germline stem cells using a human artificial chromosome", Gene Ther, 2008, 15:617-624.
Kanatsu-Shinohara et al., "Generation of Pluripotent Stem Cells from Neonatal Mouse Testis", Cell, 2004, 119:1001-1012.

(Continued)

Primary Examiner — Maria Leavitt
(74) Attorney, Agent, or Firm — Pepper Hamilton LLP

(57) ABSTRACT

A spermatogonial stem cell line that is derived from testes of rats characterized by a desirable genetic background can serve as a source for cells to transplant into male-sterile recipient animals that are immuno-compatible with the spermatogonial line. Rat cells thus transplanted readily develop into fertilization-competent, haploid male gametes, with little or no endogenous sperm competition generated by the testes of the male-sterile recipient. This approach, constituting the first vector system for the use of rat spermatogonial lines from in vitro culture in generating mutant rats on a desired genetic background, effects maximal germline transmission of donor haplotypes from the transplanted spermatogonial cells.

17 Claims, 3 Drawing Sheets

(56) References Cited

OTHER PUBLICATIONS

Nagano et al., "Transgenic mice produced by retroviral transduction of male germ-line stem cells", Proc Natl Acad Sci USA, 2001, 98:13090-13095.

Ryu et al., "Phenotypic and functional characteristics of spermatogonial stem cells in rats", Dev Biol, 2004, 274:158-170.

Hamra et al., "Isolating highly pure rat spermatogonial stem cells in culture", Methods Mol Biol, 2008, 450:163-179.

Hamra et al., "Self renewal, expansion, and transfection of rat spermatogonial stem cells in culture", Proc Natl Acad Sci USA, 2005, 102:17430-17435.

Ryu et al., "Conservation of spermatogonial stem cell self-renewal signaling between mouse and rat", Proc Natl Acad Sci USA, 2005, 102:14302-14307.

Orwig et al., "Retrovirus-mediated modification of male germline stem cells in rats", Biol Reprod, 2002, 67:874-879.

Jacob, H.J. et al., "Rat genetics: attaching physiology and pharmacology to the genome", Nature Rev. Genet, 2002, 3:33-42.

Hamra et al., "Production of transgenic rats by lentiviral transduction of male germ-line stem cells", Proc Natl Acad Sci USA, 2002, 99:14931-14936.

Hubner, N. et al., "Integrated transcriptional profiling and linkage analysis for identification of genes underlying disease", Nat Genet, 2005, 37:243-253.

Oatley, J. M. et al., "Spermatogonial stem cells", Methods Enzymol., 2006, 419:259-282.

Miller, A.D., (Cold Spring Harbor Press 1997) Retroviruses 843.

Kubota et al., "Growth factors essential for self-renewal and expansion of mouse spermatogonial stem cells", Proc Natl Acad Sci USA, 2004, 101:16489-16494.

Kanatsu-Shinohara et al., "Long-term culture of mouse male germline stem cells under serum-or feeder-free conditions", Biol Reprod, 2005, 72:985-991.

Basin et al., "Specific binding of HIV-1 nucleocapsid protein to PSI RNA in vitro requires N-terminal zinc finger and flanking basic amino acid residues", J Clin Endocrinol Metab, 1994, 79:1525-1529.

Sadeghi-Nejad et al., "Genetics of azoospermia: current knowledge, clinical implications, and future directions. Part II: Y chromosome microdeletions", Urol J, 2007, 4:192-206.

Oates et al., "Clinical characterization of 42 oligospermic or azoospermic men with microdeletion of the AZFc region of the Y chromosome, and of 18 children conceived via ICSI", Hum Reprod, 2002, 17:2813-2824.

Verma, I.M. et al., "Gene therapy—promises, problems and prospects", Nature, 1997, 389:239-242.

Ding, S. et al., "Efficient transposition of the piggyBac (PB) transposon in mammalian cells and mice", Cell, 2005, 122:473-483.

Kamtchouing et al., "Age-related changes in the function of the pituitary-gonadal axis in a sterile male rat mutant (hd/hd)", Biol. Reprod., 1991, 45:11-19.

Geens, M. et al., "Autologous spermatogonial stem cell transplantation in man: current obstacles for a future clinical application", Hum Reprod Update, 2008, 14:121-130.

Conrad, S. et al., "Generation of pluripotent stem cells from adult human testis", Nature, 2008, 456:344-349.

Hermann, B.P. et al., "Characterization, Cryopreservation, and Ablation of Spermatogonial Stem Cells in Adult Rhesus Macaques", Stem Cells, 2007, 25:2330-2338.

Kanatsu-Shinohara et al., "Production of Transgenic Rats via Lentiviral Transduction and Xenogeneic Transplantation of Spermatogonial Stem Cells", Biology of Reproduction, 2008, 79:1121-1128.

Dann et al., "Heritable and Stable Gene Knockdown in Rats", PNAS, USA, 2006, 103:11246-11251.

* cited by examiner

```
                      SEQUENCE LISTING

<160> NUMBER OF SEQ ID NOS: 19

<210> SEQ ID NO 1
<211> LENGTH: 229
<212> TYPE: DNA
<213> ORGANISM: Artificial Sequence
<220> FEATURE:
<223> OTHER INFORMATION: Sleeping Beauty 5' ITR

<400> SEQUENCE: 1
cagttgaagt cggaagttta catacactta agttggagtc attaaaactc gtttttcaac     60
tactccacaa atttcttgtt aacaaacaat agttttggca agtcagttag gacatctact    120
ttgtgcatga cacaagtcat ttttccaaca attgtttaca gacagattat ttcacttata    180
attcactgta tcacaattcc agtgggtcag aagtttacat acactaagt                229

<210> SEQ ID NO 2
<211> LENGTH: 229
<212> TYPE: DNA
<213> ORGANISM: Artificial Sequence
<220> FEATURE:
<223> OTHER INFORMATION: Sleeping Beauty ITR 3'

<400> SEQUENCE: 2
attgagtgta tgtaaacttc tgacccactg ggaatgtgat gaaagaaata aaagctgaaa     60
```

```
tgaatcattc tctctactat tattctgata tttcacattc ttaaaataaa gtggtgatcc    120
taactgacct aagacaggga attttttacta ggattaaatg tcaggaattg tgaaaaagtg   180
agtttaaatg tatttggcta aggtgtatgt aaacttccga cttcaactg              229
```

<210> SEQ ID NO 3
<211> LENGTH: 309
<212> TYPE: DNA
<213> ORGANISM: Artificial Sequence
<220> FEATURE:
<223> OTHER INFORMATION: Piggybac ITR 5'

<400> SEQUENCE: 3

```
ccctagaaag atagtctgcg taaaattgac gcatgcattc ttgaaatatt gctctctctt    60
tctaaatagc gcgaatccgt cgctgtgcat ttaggacatc tcagtcgccg cttggagctc   120
ccgtgaggcg tgcttgtcaa tgcggtaagt gtcactgatt ttgaactata acgaccgcgt   180
gagtcaaaat gacgcatgat tatcttttac gtgactttta agatttaact catacgataa   240
ttatattgtt atttcatgtt ctacttacgt gataacttat tatatatata ttttcttgtt   300
atagatatc                                                          309
```

<210> SEQ ID NO 4
<211> LENGTH: 238
<212> TYPE: DNA
<213> ORGANISM: Artificial Sequence
<220> FEATURE:
<223> OTHER INFORMATION: Piggybac ITR 3'

<400> SEQUENCE: 4

```
taaaagtttt gttactttat agaagaaatt ttgagttttt gttttttttt aataaataaa    60
taaacataaa taaattgttt gttgaattta ttattagtat gtaagtgtaa atataataaa   120
acttaatatc tattcaaatt aataaataaa cctcgatata cagaccgata aaacacatgc   180
gtcaatttta cgcatgatta tctttaacgt acgtcacaat atgattatct ttctaggg     238
```

<210> SEQ ID NO 5
<211> LENGTH: 35
<212> TYPE: DNA
<213> ORGANISM: Artificial Sequence
<220> FEATURE:
<223> OTHER INFORMATION: transposon fragment 1

<400> SEQUENCE: 5

```
ccctagaaag atagtctgcg taaaattgac gcatg                              35
```

<210> SEQ ID NO 6
<211> LENGTH: 63
<212> TYPE: DNA
<213> ORGANISM: Artificial Sequence
<220> FEATURE:
<223> OTHER INFORMATION: transposon fragment 2

<400> SEQUENCE: 6

```
catgcgtcaa ttttacgcat gattatcttt aacgtacgtc acaatatgat tatctttcta    60
ggg                                                                 63
```

<210> SEQ ID NO 7
<211> LENGTH: 22
<212> TYPE: DNA
<213> ORGANISM: Artificial Sequence
<220> FEATURE:
<223> OTHER INFORMATION: EGFP primer 5'

<400> SEQUENCE: 7
gtctcgtgac cctgacctac gg                                    22

<210> SEQ ID NO 8
<211> LENGTH: 21
<212> TYPE: DNA
<213> ORGANISM: Artificial Sequence
<220> FEATURE:
<223> OTHER INFORMATION: EGFP primer 3'

<400> SEQUENCE: 8
atgcccttca gctcgatgcg g                                     21

<210> SEQ ID NO 9
<211> LENGTH: 20
<212> TYPE: DNA
<213> ORGANISM: Artificial Sequence
<220> FEATURE:
<223> OTHER INFORMATION: GAPDH primer 5'

<400> SEQUENCE: 9
atgattctac ccacggcaag                                       20

<210> SEQ ID NO 10
<211> LENGTH: 20
<212> TYPE: DNA
<213> ORGANISM: Artificial Sequence
<220> FEATURE:
<223> OTHER INFORMATION: GAPDH primer 3'

<400> SEQUENCE: 10
gctaagcagt tggtggtgca                                       20

<210> SEQ ID NO 11
<211> LENGTH: 18
<212> TYPE: DNA
<213> ORGANISM: Artificial Sequence
<220> FEATURE:
<223> OTHER INFORMATION: LTR primer 5'

<400> SEQUENCE: 11
aacagggact tgaaagcg                                         18

<210> SEQ ID NO 12
<211> LENGTH: 20
<212> TYPE: DNA
<213> ORGANISM: Artificial Sequence
<220> FEATURE:
<223> OTHER INFORMATION: LTR primer 3'

<400> SEQUENCE: 12
atactgacgc tctcgcaccc                                       20

<210> SEQ ID NO 13
<211> LENGTH: 24
<212> TYPE: DNA
<213> ORGANISM: Artificial Sequence
<220> FEATURE:
<223> OTHER INFORMATION: LacZ primer 1

<400> SEQUENCE: 13
cgattaagtt gggtaacgcc aggg                                  24

<210> SEQ ID NO 14
<211> LENGTH: 35
<212> TYPE: DNA

```
<213> ORGANISM: Artificial Sequence
<220> FEATURE:
<223> OTHER INFORMATION: BalT primer 1

<400> SEQUENCE: 14
cttgtcatga attgtgatac agtgaattat aagtg                              35

<210> SEQ ID NO 15
<211> LENGTH: 24
<212> TYPE: DNA
<213> ORGANISM: Artificial Sequence
<220> FEATURE:
<223> OTHER INFORMATION: LacZ primer 2

<400> SEQUENCE: 15
ttctgcttca tcagcaggat atcc                                          24

<210> SEQ ID NO 16
<211> LENGTH: 24
<212> TYPE: DNA
<213> ORGANISM: Artificial Sequence
<220> FEATURE:
<223> OTHER INFORMATION: LacZ primer 3

<400> SEQUENCE: 16
accacgctca tcgataattt cacc                                          24

<210> SEQ ID NO 17
<211> LENGTH: 25
<212> TYPE: DNA
<213> ORGANISM: Artificial Sequence
<220> FEATURE:
<223> OTHER INFORMATION: Tbc1d1 P1 primer

<400> SEQUENCE: 17
atcacttgtg agcacgcagg gaata                                         25

<210> SEQ ID NO 18
<211> LENGTH: 21
<212> TYPE: DNA
<213> ORGANISM: Artificial Sequence
<220> FEATURE:
<223> OTHER INFORMATION: ZRT primer 1

<400> SEQUENCE: 18
gattgaccgt aatgggatag g                                             21

<210> SEQ ID NO 19
<211> LENGTH: 25
<212> TYPE: DNA
<213> ORGANISM: Artificial Sequence
<220> FEATURE:
<223> OTHER INFORMATION: Tbc1d1-P2  primer

<400> SEQUENCE: 19
aagggaaggg agggcatcta gtcct                                         25
```

PRODUCTION AND USE OF RAT SPERMATOGONIAL STEM CELL LINES

STATEMENT REGARDING FEDERALLY SPONSORED RESEARCH OR DEVELOPMENT

This invention was made with government support under Grant Number 5R21RR023958-02 awarded by the National Institute of Health/National Center for Research Resources (NIH/NCRR). The U.S. Government has certain rights in the invention.

CROSS-REFERENCE TO RELATED PATENT APPLICATIONS

This application is the U.S. National Stage filing of International Application Serial No. PCT/US2009/066275, filed Dec. 1, 2009, which claims the benefit of U.S. Provisional Application No. 61/119,005, filed Dec. 1, 2008 and U.S. Provisional Application No. 61/187,498, filed Jun. 16, 2009, each of which are herein incorporated by reference in their entireties.

BACKGROUND OF THE INVENTION

The present invention relates generally to the stem cell field and, more particularly, to employing stem cells in the development of rat cell lines and animals.

Propagation of Spermatogonial Stem Cell Lines

The ability to conditionally induce the development of stem cell lines through the process of spermatogenesis in vitro for the production of gametes would provide a long-sought-after technology for biomedical research, particularly if such protocols could be established for a variety of species. The discovery that stem cells residing within fractions of dissociated mouse and rat testis cells maintain their ability to regenerate spermatogenesis in testes of recipient mice was essential to establishing such culture systems. See Brinster et al., *Proc Natl Acad Sci USA* 1994; 91:11303-11307; Brinster et al., *Proc Natl Acad Sci USA* 1994; 91:11298-11302; Clouthier et al., *Nature* 1996; 381:418-421; Kanatsu-Shinohara et al., *Biol Reprod* 2003; 69:612-616; and Nagano et al., *Tissue Cell* 1998; 30:389-397. The ability to isolate and experimentally manipulate these stem cells has opened new doors for research on spermatozoan development, assisted reproduction, cellular therapy and genetics. See Nagano et al., *Biol Reprod* 1999; 60:1429-1436; Mahato et al., *Endocrinology* 2000; 141:1273-1276; Mahato et al., *Mol Cell Endocrinol* 2001; 178:57-63; Ogawa et al., *Nat Med* 2000; 6:29-34; Shinohara et al., *Proc Natl Acad Sci USA* 2006; 103: 13624-13628; Zhang et al., *J Cell Physiol* 2007; 211:149-158; Kazuki et al., *Gene Ther* 2008; 15:617-624; Kanatsu-Shinohara et al., *Cell* 2004; 119:1001-1012; Kanatsu-Shinohara et al., *Proc Natl Acad Sci USA* 2006; 103:8018-8023; and Nagano et al., *Proc Natl Acad Sci USA* 2001; 98:13090-13095. In view of this potential, protocols for isolating, propagating and genetically modifying fully functional rat spermatogonial stem cells in culture have been established. See Ryu et al., *Dev Biol* 2004; 274:158-170; Hamra et al., *Dev Biol* 2004; 269:393-410; Hamra et al., *Proc Natl Acad Sci USA* 2002; 99:14931-14936; Hamra et al., *Methods Mol Biol* 2008; 450:163-179; Hamra et al., *Proc Natl Acad Sci USA* 2005; 102:17430-17435; Ryu et al., *Proc Natl Acad Sci USA* 2005; 102:14302-14307; Orwig et al., *Biol Reprod* 2002; 67:874-879; and Kanatsu-Shinohara et al., *Biol Reprod* 2008. The rat was chosen as a species for these studies due to its popularity as a laboratory animal model for the study of human health and disease, and due to the lack of protocols for genetically modifying the rat germline using clonally expanded stem cells from culture. See Hamra et al., *Proc Natl Acad Sci USA* 2002; 99:14931-14936 Considering the many potential applications of the laboratory rat as a research model, a cost-effective and easy-to-prepare culture medium was sought in this study for the derivation and continuous proliferation of primary rat spermatogonial stem cell lines in vitro.

In respect of this goal, media previously reported for long-term proliferation of rodent spermatogonial stem cells in vitro represent clear methodological advances for studies on the biology and applications of spermatogonia. See Kanatsu-Shinohara et al., *Biol Reprod* 2003; 69:612-616; Hamra et al., *Proc Natl Acad Sci USA* 2005; Ryu et al., *Proc Natl Acad Sci USA* 2005; 102:14302-14307; Kubota et al., *Proc Natl Acad Sci USA* 2004; 101:16489-16494; and Kanatsu-Shinohara et al., *Biol Reprod* 2005; 72:985-991. However, such media are relatively complex, expensive, time-consuming to prepare, plus are most effective when applied in combination with feeder layers of fibroblasts. See id. For example, the medium originally reported by Shinohara and colleagues for the successful derivation and long-term cultivation of germline stem cells from postnatal mouse testes was a pivotal breakthrough in spermatogonial research. See Kanatsu-Shinohara et al., *Biol Reprod* 2003; 69:612-616. However, Shinohara's medium is based on the proprietary, StemPro-34 medium, plus 24 individually added components, including small molecules, fetal bovine serum and a mixture of polypeptide growth factors. Serum-free derivatives of Shinohara's medium have since been formulated for spermatogonial culture, in which the serum has been replaced by the supplement, B-27. See Hamra et al., *Proc Natl Acad Sci USA* 2005; 102: 17430-17435 and Kanatsu-Shinohara et al., *Biol Reprod* 2005; 72:985-991. Upon inspection of components within B-27 supplement we postulated that it could be used together with key growth factors in a commonly applied nutrient mixture to formulate a more efficient spermatogonial culture medium.

Sterile Testes Complementation

Currently, specific causes of infertility in men remain a mystery in 40-60% of cases. See Bhasin et al., *J Clin Endocrinol Metab* 79, 1525-9 (1994); Sadeghi-Nejad et al., *Urol J* 4, 192-206 (2007); and Matzuk et al., *Nat Med* 14, 1197-213 (2008). In total, >5% of the male population is infertile, and >1% of all males are inflicted with a severe defect in sperm production termed azoospermia. See Bhasin et al., *J Clin Endocrinol Metab* 79, 1525-9 (1994); Sadeghi-Nejad et al., *Urol J* 4, 192-206 (2007); Barthold et al. *J Urol* 170, 2396-401 (2003); and Bleyer, W. A. *CA Cancer J Clin* 40, 355-67 (1990). Fundamentally, because azoospermia results in an inability to reproduce by natural mating, it seems enigmatic as to why this disease remains so prevalent in the human population. Such an epidemiological trend clearly points to the existence of potent environmental factors that disrupt the process of sperm production (i.e. spermatogenesis) or a substantial number of de novo mutations that could arise during a lifetime to render one sterile, but otherwise healthy. See Bhasin et al., *J Clin Endocrinol Metab* 79, 1525-9 (1994); Bleyer, W. A., *CA Cancer J Clin* 40, 355-67 (1990); Reijo, R. et al. *Nat Genet.* 10, 383-93 (1995); Oates et al., *Hum Reprod* 17, 2813-24 (2002). In fact, this is true in numerous cases, as such de novo mutations account for several types of male-factor infertility already defined at a genetic level and increasing numbers of males are left infertile during their childhood by cancer chemotherapy. See Sadeghi-Nejad, et al., *Urol J* 4, 192-206 (2007); Reijo et al. *Nat Genet.* 10, 383-93 (1995);

Bleyer et al., *CA Cancer J Clin* 40, 355-67 (1990); Oates et al., *Hum Reprod* 17, 2813-24 (2002); Bhasin, S., *J Clin Endocrinol Metab* 92, 1995-2004 (2007); and Geens, M. et al., *Hum Reprod Update* 14, 121-30 (2008). As a new hope for many infertile men with azoospermia, a pioneering breakthrough in stem cell biology that manifested strong links between reproductive biology and genetic research was the discovery that mouse testes contained spermatogonial stem cells capable of generating fully functional sperm following isolation and transplantation into testes of another mouse. See Brinster & Zimmermann, *Proc Natl Acad Sci USA* 91, 11298-302 (1994). Similar experiments soon followed in rats, and isolated mouse spermatogonia were next shown to maintain their regenerative potential after months in culture. See Clouthier et al., *Nature* 381, 418-21 (1996); Nagano et al., *Tissue Cell* 30, 389-97 (1998). New culture media supporting the long term proliferation of rodent spermatogonial lines in vitro have since been formulated and scientists are now on the brink of establishing conditions required to cultivate human spermatogonial lines from testis biopsies. See Kanatsu-Shinohara et al., *Biol Reprod* 69, 612-6 (2003); Hamra, F. K. et al., *Proc Natl Acad Sci USA* 102, 17430-5 (2005); Conrad, S. et al. *Nature* (2008); and Kossack, N. et al. "Isolation and Characterization of Pluripotent Human Spermatogonial Stem Cell-Derived Cells." *Stem Cells* (2008). Ostensibly, the ability to propagate spermatogonial lines in culture, prior to using them to produce functional spermatozoa by transplanting them back into the testes of their own donor, presents a clear strategy to cure many existing types of male infertility. Due in large part to the multipotent nature of germline stem cells however, before these breakthroughs are translated into practice it is imperative that preclinical details of such cellular therapies first be stringently evaluated in more advanced, non-human recipients of medical relevance. See Geens, M. et al., *Hum Reprod Update* 14, 121-30 (2008); Conrad, S. et al. "Generation of pluripotent stem cells from adult human testis." *Nature* (2008); Kossack, N. et al. "Isolation and Characterization of Pluripotent Human Spermatogonial Stem Cell-Derived Cells." *Stem Cells* (2008); Hermann, B. P. et al. *Stem Cells* 25, 2330-8 (2007); and Zhang et al., *J Cell Physiol* 211, 149-58 (2007).

Production of Transgenic Animals

In mice, embryonic stem (ES) cell-based knockout technology is very efficient for single gene targeting, and it can be combined as well with the usage of random mutagens, such as chemical mutagenic agents, viruses or transposons, for the large-scale generation of ES cell libraries, carrying different molecularly marked knockout alleles. These ES cell clones can be used for the production of knockout mice.

While this methodology is applicable for mice, it cannot be employed with rats or with other laboratory animals. Furthermore, no similar or equivalent techniques to the mouse ES cell technique have yet been developed that would be applicable to a variety of animal models and not limited to one animal species like the ES cell technique in mice. For example, due to the above-mentioned technical limitation very few rat knockout strains are currently existing worldwide. This may at least partially be the result of the practicability of random mutagenesis in animals, which has proven to be questionable for several reasons. For example, the requirement of a large number of offspring, the time for rearing offspring, the costs of establishing and maintaining large-scale animal facilities are some of the factors to be considered when generating transgenic animals using random mutagenesis in animals. Accordingly, there exists a need for more advantageous methods of targeted mutagenesis that can be applied in a variety of animal models and are more practicable.

Current technologies used to create transgenic rats require a high level of expertise and are costly to produce. Additionally, there are many disadvantages to the currently available recipient rat models for testicular transplantation of donor stem cells. These disadvantages include but are not limited to: (1) lower germline transmission from the donor cells to progeny, due to high levels of competition from endogenous sperm cell production; (2) the need for a high number of stems cells to be transplanted into recipient testes to produce transgenic progeny; (3) a large number of progeny must be produced to yield the desired mutant rat line; and (4) the need for a high dose of cytotoxic chemicals or irradiation to achieve effective engraftment of testes by donor stem cells. In conventional protocols, moreover, the most effective levels of stem cell engraftment have not been realized because lethal doses of irradiation or cytotoxic reagents required for effective stem cell engraftment kill the recipients. Finally, production of rat lines with loss or gain of function gene mutations requires tedious, time-consuming and prohibitively expensive micromanipulation of embryos.

There is a general need to annotate the human genome with function, linking laboratory animals into this process is a necessary requirement for accelerating improvements in health care. For example, extensive phenotyping and detailed analysis of inbred animals strains has resulted in the localization of hundreds of loci involved in complex diseases. These "quantitative trait loci" (QTLs) demonstrate genetic linkage to many disease traits which are shared between laboratory animals, such as rats, and humans. Examples for such diseases include hypertension, neuronal regeneration, ischemic cerebrovascular and cardiovascular diseases, and diabetes. See Jacob, H. J. et al., *Nature Rev. Genet.* 3:33 (2002), and Hubner, N. et al., loc. cit. 37:243 (2005).

SUMMARY OF THE INVENTION

The claimed invention comprehends, in part, using certain naturally occurring or transgenically generated ("genetically") male-sterile rats as recipients for donor sperm stem cells with which the rats also are immuno-compatible. Spermatogenesis in these rats is severely disrupted, but they maintain a functional stem cell compartment. Accordingly, the transplanted sperm stem cells are free to develop into functional spermatozoa and to fertilize female rats in the absence of competition from sperm that also would be produced, were the recipients male-fertile. In this manner, 100% germline transmission of the donor cell haplotype can be achieved from a relatively low number of transplanted sperm stem cells.

Thus, pursuant to one aspect of the present invention, a methodology is provided for effecting germline transmission of a rat donor haplotype. The inventive method comprises the steps of (A) providing cells of a spermatogonial stem cell line that is derived from rat testes, which cell line embodies a predetermined genetic background, and then (B) transplanting one or more of the cells into a male-sterile recipient rat that can be, for example, the product of crossing a DAZL-deficient transgenic rat into the aforementioned genetic background, the recipient rat being immuno-compatible with the cells, such that transplanted cells develop into fertilization-competent, haploid male gametes.

In accordance with another aspect of the invention, a library is provided of cells of a spermatogonial stem cell line that is derived from rat testes. A library of the invention contains a plurality of transposon-mediated gene knockout or "knockin" mutant stem cells.

In accordance with an additional aspect of the invention, a medium for growing spermatogonial stem cells is provided, in addition to methods for culturing spermatogonial stem cells.

Figure 1:
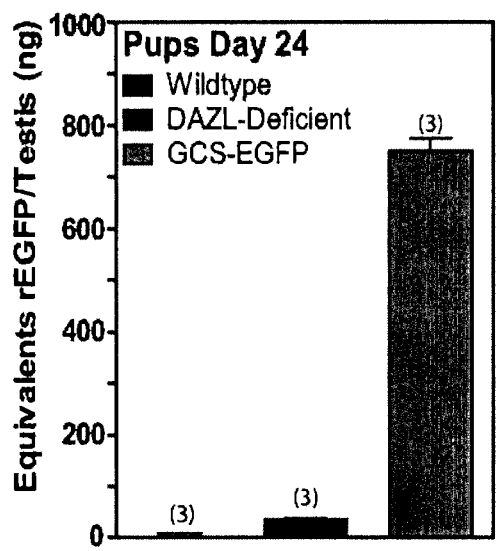
FIG. 1. DAZL-Deficient Rat Testes are Effectively Colonized by Donor Spermatogonia. (A) Relative abundance of EGFP in testes of Wildtype, DAZL-deficient and GCS-EGFP rats. Left: Data expressed as the equivalents of recombinant, histidine-tagged EGFP (rEGFP)/testis (+/−SEM, n=3 testes/rat strain) as determined by fluorometry of testis extracts at 24 days of age. Right: Bright field (top) and green fluorescence (bottom) images of testes dissected from wildtype (WT), DAZL-deficient (Dazl-Def) and GCS-EGFP rats at 24 days of age. Scale bar=1 cm. (B) Spermatogenesis colony forming assays using DAZL-deficient rats as recipients. Left: Numbers of spermatogenic colonies formed/testis by donor GCS-EGFP rat spermatogonia in Wildtype (10.25+/−0.68 colonies/testis, +/−SEM, n=8 testes) and DAZL-Deficient rats (30.69+/−0.62 colonies/testes, +/−SEM, n=8 testes) at 30 days following transplantation. Donor spermatogonia were transplanted at passages 15 and 17 (i.e. culture days 182 and 204) at 2000 GCS-EGFP$^+$ cells/testis. Right: Images of individual colonies of spermatogenesis in Wildtype and DAZL-deficient recipient rats that were generated by the donor GCS-EGFP spermatogonia (green fluorescence is from donor cells). Images are representative of colonies scored and plotted in the Left panel. Scale bar=100 μm.
Figure 1:
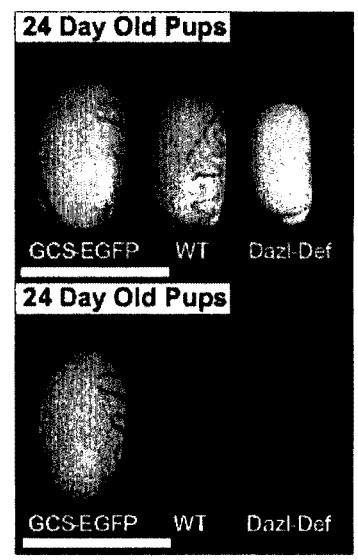
Figure 1:
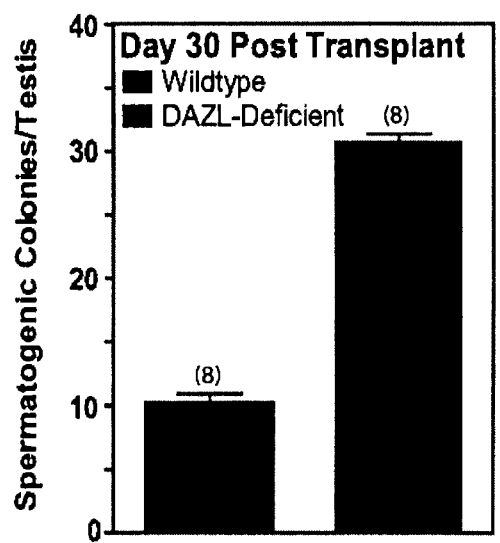
Figure 1:
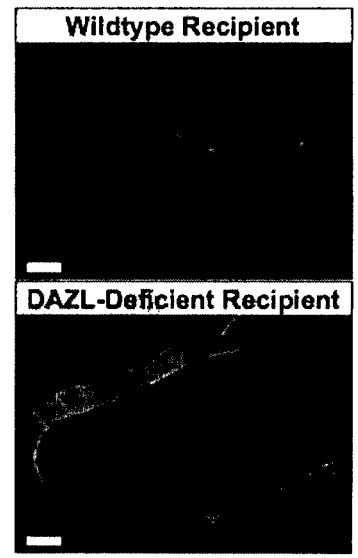

Table 1. Progeny from Wildtype and DAZL-Deficient recipient rats transplanted with GCS-EGFP rat spermatognia Table 2. Components of Rat Spermatogonial Culture Media Table 3. Vendor and Catalog numbers for SA and SG media components

DETAILED DESCRIPTION OF THE PREFERRED EMBODIMENTS

Inventors have achieved virtually 100% germline transmission to rat progeny by mating from donor primary lines of rat spermatogonial stem cells, following their propagation in culture, cryopreservation in liquid nitrogen, thawing, further expansion in culture, transplantation into the testes of recipient, male-sterile rats, and development into functional spermatozoa.

Rat spermatogonial stem cells are rat cell types that when transplanted into the testes can develop into fertilization competent haploid gametes, such as spermatids or spermatozoa. Natural mating or breeding of the recipient with a female rat bypasses any requirement for assisted fertilization methods. Additionally, mating can include methods such as but not limited to in vitro fertilization, intrauterine transfer, or oocyte injection with nuclei. Sperm produced from the spermatogonial lines in the recipient rats are highly effective at transmitting the donor haplotype to F1 and F2 progeny by mating, thereby rendering unnecessary conventional embryo manipulations to generate rat progeny from donor spermatogonial lines.

Pursuant to the invention, therefore, the combination of (i) rat spermatogonial lines that can be propagated in culture and (ii) male-sterile recipient rats is an optimal vector for germline transmission of natural or genetically modified rat genomes. This approach will allow for preservation of existing rat lines and the production of new transgenic rat lines important for science and industry. For example, the invention offers avenues to the establishment of new transgenic mutant rat models, for the study of human biology and disease.

In accordance with the invention, spermatogonial stem cell lines are derived from testes of rats, such as inbred Fischer 344 rats, that embody a desirable genetic background. The derived lines are expanded in cell number over subsequent subculturing steps in vitro, preferably using SG medium, which is described below. Furthermore, DAZL-deficient transgenic rats are obtained from a cross into the desired rat genetic (e.g., Fischer 344) background. The male-sterile recipient animals thus produced are immuno-compatible with the derived spermatogonial lines.

The phrase "spermatogonial stem cells" in this description denotes stem cells isolated from the testis. Spermatogonial stem cells are incapable of fertilizing an egg cell but can give rise to cells that develop into sperm and that produce viable offspring. Isolated spermatogonial stem cells can be cultured for a prolonged time period without losing their properties and can efficiently repopulate the testes of suitable recipient male animals described, for instance, in Oatley J. M. et al., *Methods Enzymol.* 419:259 (2006).

Pursuant to the invention, transplanting cells of a spermatogonial line, as described above, into an immuno-compatible, male-sterile recipient allows the cells to develop into fertilization-competent, haploid male gametes. Since there is negligible endogenous sperm competition generated by the testes of the male-sterile recipient's testes, the inventive approach effects maximal germline transmission of donor haplotypes from the transplanted spermatogonial cells.

Accordingly, the present invention provides the first vector system for employing rat spermatogonial lines from in vitro culture in generating mutant rats on a desired genetic background. The inventive approach allows for more cost-effective production of mutant/transgenic/chimeric rat lines and rat cell lines of a pure/inbred genetic background, illustrated by Fischer 344. In relation to the latter, by way of example, such production can be accomplished using either the Fischer rat spermatogonia themselves or pluripotent Fischer rat stem cell lines derived directly from the spermatogonia.

A pure genetic background, thus achievable with the present invention, is more desirable than a mixed genetic background for testing the effects of gene mutations and transgenes in animal studies. Moreover, conventional production of rat lines with loss- or gain-of-function mutations requires tedious, time-consuming, and prohibitively expensive micromanipulation of embryos.

By contrast, the inventive approach can use spermatogonia from inbred rats to bypass any requirement for in vitro manipulating of early rat embryos of inbred strains. This reduces the time, cost, and effort required to produce mutations in inbred or outbred rat lines.

In particular, the invention enables the production of highly complex spermatogonial libraries, for use as vectors for large-scale production of mutant rat lines in a desired, preferably inbred genetic background. Such mutant libraries of the invention open the way for producing a wider variety of mutant rats, with disrupted genes in an inbred genetic background, at orders-of-magnitude faster rates and at a lower per-animal cost than current approaches can accommodate. Additionally, the invention affords a source of pluripotent rat stem cells, which can be used in place of rat embryonic stem cells and which is accessible without the need for special skills to manipulate the early rat embryo.

Mutant libraries can be generated, in accordance with the invention, through the use of DNA transposons. DNA transposons can be viewed as natural gene delivery vehicles that integrate into the host genome via a "cut-and-paste" mechanism. These mobile DNA elements encode a transposase flanked by inverted terminal repeats (ITRs) that contain the transposase binding sites necessary for transposition. Any gene of interest flanked by such ITRs can undergo transposition in the presence of the transposase supplied in trans.

As noted, a "transposon" is a segment of DNA that can move (transpose) within the genome. A transposon may or may not encode the enzyme transposase, necessary to catalyze its relocation and/or duplication in the genome. Where a transposon does not code for its transposase enzyme, expression of said enzyme in trans may be required when carrying out the method of the invention in cells not expressing the relevant transposase itself Furthermore, a transposon must contain sequences that are required for its mobilization, namely the terminal inverted repeats containing the binding sites for the transposase. The transposon may be derived from a bacterial or a eukaryotic transposon. Further, the transposon may be derived from a class I or class II transposon. Class II or DNA-mediated transposable elements are preferred for gene transfer applications, because transposition of these elements does not involve a reverse transcription step, which pertains in transposition of Class I or retro-elements and which can introduce undesired mutations into transgenes. For example, see Miller, A. D., RETROVIRUSES 843 (Cold Spring Harbor Laboratory Press, 1997), and Verma, I. M. et al., *Nature* 389:239 (1997).

Transposons also can be harnessed as vehicles for introducing "tagged" genetic mutations into genomes, which makes such genomic sites of transposon integration/mutation easy to clone and defined at the DNA sequence level. This fact makes transposon-based technology especially attractive in cultures of germline stem cells derived from a variety of model species, including the laboratory rat. For example, the first mutagenesis screens in mammals have established that Sleeping Beauty can generate a high number of random mutations in both mouse and rat germinal cells in vivo. Alternatively, where mutagenic events can first be selected and then used to produce experimental animal models, random mutagenesis would be more feasible in tissue culture.

Similarly, transposons can be harnessed as vehicles for introducing mutations into genomes. Specifically, genes may be inactivated by transposon insertion. For example, such genes are then "tagged" by the transposable element, which can be used for subsequent cloning of the mutated allele. In addition to gene inactivation, a transposon may also introduce a transgene of interest into the genome if contained between its ITRs. Moreover, to insert or knockin a DNA construct or gene of interest into an existing site of transposition, stem cell lines or animals produced with transposons are designed to contain recognition sequences (e.g., pLox sties) within the transposon that act as substrates for DNA recombinase enzymes (e.g., Cre-recombinase). This would allow a gene of interest flanked by compatible recombinase recognition sequences to be delivered into the cells or animals in trans with a recombinase to catalyze integration of the gene of interest into the genomic locus of the transposon. The transposon may carry as well the regulatory elements necessary for the expression of the transgene, allowing for successful expression of the gene.

Examples of transposon systems that can transpose in vertebrates have recently became available, such as Sleeping Beauty, piggyBac, Tol2 or Frog Prince. Each transposon system can be combined with any gene trap mechanism (for example: enhancer, promoter, polyA, or slice acceptor gene traps) to generate the mutated gene, as discussed below. Sleeping Beauty (SB) and Frog Prince (FP) are Tc1 transposons, whereas piggyBac (PB) was the founder of the PB transposon family and Tol2 is a hAT transposon family member. Both the Sleeping Beauty and the Frog Prince transposon are found in vertebrates as inactive copies, from which active transposon systems have been engineered. The Tol2 transposon also has been found in vertebrates as an active transposon.

The piggyBac transposon was originally found as an active transposon in insects but was subsequently shown to have high levels of activity in vertebrates, too, as shown in Ding S et al., *Cell* 122:473 (2005). Each of these elements has their own advantages; for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore mutagenise overlapping, but distinct sets of genes. Therefore, to achieve the best possible coverage of genes, the use of more than one element is particularly preferred.

In addition to naturally occurring transposons, modified transposon systems such as those disclosed in European patent documents EP1594973, EP1594971, and EP1594972 also may be employed in this invention. Preferably, the transposons used for the method of the invention possess highly elevated transpositional activity.

In a preferred embodiment of the present invention, the transposon is a eukaryotic transposon, such as the Sleeping Beauty transposon, the Frog Prince transposon, the piggyBac transposon, or the Tol2 transposon, as discussed above.

The use of gene-trap constructs for insertional mutagenesis in tissue culture, where trapped events can easily be selected for, is advantageous over the random mutagenesis in animals. Gene trap vectors report both the insertion of the transposon into an expressed gene, and have a mutagenic effect by truncating the transcript through imposed splicing. Cells selected for a particular gene trap event can be used for the generation of animal models lacking this specific genetic function.

When transposons are used in insertional mutagenesis screens, transposon vectors typically constitute four major classes of constructs, suitable for identifying mutated genes rapidly. These contain a reporter gene, which should be expressed depending on the genetic context of the integration. Specific gene traps include, but are not limited to: (1) enhancer traps, (2) promoter traps, (3) polyA traps, and (4) splice acceptor traps. In enhancer traps, the expression of the reporter requires the presence of a genomic cis-regulator to act on an attenuated promoter within the integrated construct. Promoter traps contain no promoter at all. These vectors are only expressed if they land in-frame in an exon or close downstream to a promoter of an expressed gene. In polyA traps, the marker gene lacks a polyA signal, but contains a splice donor (SD) site. Thus, when integrating into an intron, a fusion transcript can be synthesized comprising the marker and the downstream exons of the trapped gene. Slice acceptor gene traps (or exon traps) also lack promoters, but are equipped with a splice acceptor (SA) preceding the marker gene. Reporter activation occurs if the vector is integrated into an expressed gene, and splicing between the reporter and an upstream exon takes place. The splice acceptor gene trap and polyA gene trap cassettes can be combined. In that case, the marker of the polyA trap part is amended with a promoter so that the vector also can trap downstream exons, and both upstream and downstream fusion transcripts of the trapped gene can be obtained. The foregoing constructs also offer the possibility to visualize spatial and temporal expression patterns of the mutated genes by using, e.g., LacZ or fluorescent proteins as a marker gene.

Accordingly, the present invention comprehends a method based on the combination of transposon-mediated insertional mutagenesis with a tissue culture system, namely, with rat spermatogonial stem cells, which allows for the ready generation of in vitro spermatogonial stem cell libraries carrying a large number of different insertion events. Compared to classical nuclear transfer technologies and in vivo mutagenesis, moreover, this method is less costly and less labor-intensive, and it allows for the selection of the appropriate insertion(s) before establishing the corresponding animal models. Additionally, using these cells or libraries allows for establishment of a broader variety of animal models.

As noted above, the phrase "quantitative trait loci" (QTLs) denotes the localization of multiple loci involved in complex diseases and quantitative phenotypes. Certain QTLs demonstrate genetic linkage to many disease traits that are shared between rats and humans.

A quantitative trait locus may be further mutated using the "local hopping" property of transposons. A transposon insertion site can be remobilized by the expression of the transposase recognizing the transposon elements responsible for mediating the excision either in spermatogonial stem cells in culture or at a later stage in vivo.

Libraries of spermatogonial cell lines can be generated by isolating and then pooling individual clonal lines with mutated genes. First, spermatogonial lines are genetically modified with a DNA construct that harbors a selectable marker, such as a gene encoding resistance to G418. Then, due to stable integration of the DNA construct into different locations within the genome, a mixed population of genetically distinct clonal spermatogonial lines is selected using the selectable marker. By pooling these selected individual clonal lines with mutated genes, a library of mutant rat spermatogonia is generated.

In order to transmit stem cell genomes through the rat germline, spermatogonial lines containing gene trap Sleeping Beauty insertions, for example, can be selected in culture and transplanted to repopulate testes of sterile recipient rats. Thus, the testes of DAZL-deficient and wild-type recipient rats can be transplanted with mixed populations of a selectably-resistant spermatogonial line, such as G418, selected as a library estimated to contain ~200,000 individual clonal lines with trapped genes (see Example 5 below).

The phrase "selectable marker" is employed here to denote a protein that enables the separation of cells expressing the marker from those that lack or do not express it. The selectable marker may be a fluorescent marker, for instance.

Expression of the marker by cells having successfully integrated the transposon allows the isolation of these cells using methods such as, for example, FACS (fluorescent activated cell sorting). Alternatively, expression of a selectable marker may confer an advantageous property to the cell that allows survival of only those cells carrying the gene.

For example, the marker protein may allow for the selection of the cell by conferring an antibiotic resistance to the cell. Consequently, when cells are cultured in medium containing said antibiotic, only cell clones expressing the marker protein that mediates antibiotic resistance are capable of propagating. By way of illustration, a suitable marker protein may confer resistance to antibiotics such as ampicillin, kanamycin, chloramphenicol, tetracycline, hygromycin, neomycin or methotrexate. Further examples of antibiotics are penicillins: ampicillin HCl, ampicillin Na, amoxycillin Na, carbenicillin disodium, penicillin G, cephalosporins, cefotaxim Na, cefalexin HCl, vancomycin, cycloserine. Other examples include bacteriostatic inhibitors such as: chloramphenicol, erythromycin, lincomycin, spectinomycin sulfate, clindamycin HCl, chlortetracycline HCl. Additional examples are marker proteins that allow selection with bactericidal inhibitors such as those affecting protein synthesis irreversibly causing cell death, for example aminoglycosides such as gentamycin, hygromycin B, kanamycin, neomycin, streptomycin, G418, tobramycin. Aminoglycosides can be inactivated by enzymes such as NPT II which phosphorylates 3'-OH present on kanamycin, thus inactivating this antibiotic. Some aminoglycoside modifying enzymes acetylate the compounds and block their entry in to the cell. Marker proteins that allow selection with nucleic acid metabolism inhibitors like rifampicin, mitomycin C, nalidixic acid, doxorubicin HCl, 5-fluorouracil, 6-mercaptopurine, antimetabolites, miconazole, trimethoprim, methotrexate, metronidazole, sulfametoxazole are also examples for selectable markers.

The term "rat" refers to a member of the genus Rattus, such as the black rat, Rattus rattus, and the brown rat, Rattus norvegicus. The laboratory rat is one of the most extensively studied model organisms for human disease and, hence, is the major animal model in the initial stages of drug development. In contrast to mice, a limitation of the rat model has been the lack of technology for generating "defined" genetic mutants. Such defined genetic mutants, where precise changes to a gene sequence or function are made without perturbing the rest of the genome, are critical for determining gene function with a high degree of certainty and for creating reliable genetic models for human disease. Due to the lack of technology for generating defined mutants in rats, genetic manipulation approaches were not successful in the rat genome so far and genome research in the rat to connect genetic backgrounds with certain phenotypes is lagging behind.

Once generated, a spermatogonial cell line is transplanted into a male-sterile recipient rat. In a preferred embodiment of the invention, spermatogonial cell lines are transplanted into transgenically created male-sterile recipients. Alternatively, spermatogonial cell lines are transplanted into recipients that have naturally occurring genetic mutations that cause male-sterility.

Examples of naturally occurring mutations that generate male sterile rats include but are not limited to: rats that have mutations in FKBP6; rats that have altered function of the pituitary-gonadal axis, see Kamtchouing et al. Biol. Reprod. 45:11-19 (1991), for example; and rats that have a mutant BIL/1. Illustrative of transgenically generated male sterile rat are the DAZL-deficient transgenic rat and rats that express the HSV type 1 thymidine kinase protein.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods and maintain the viability of the spermatogonial stem cell line.

As used herein, the terms "fragment" and "fragment of a transposon" are meant to refer to DNA sequences which are not complete transposon DNA sequences (i.e. full-length DNA sequences) but DNA sequences shorter in length than the full-length sequence which consist of nucleotide sequences identical to nucleotide sequences of portions of a full-length DNA sequence of a transposon. A fragment of a transposon may function like a full length DNA. In some embodiments, a fragment of a transposon is a truncated form of the wild-type or full-length DNA transposon sequence. In some embodiments a fragment of a transposon is an internal tandem repeat of the transposon. For example, in some embodiments where compositions or methods comprise transplanted haplotypes, the haplotypes comprise fragments of full-length transposons that flank transgenes of mutated genes of interest. In some embodiments, the transplanted haplotypes comprise at least one or more of any combination of the fragments of a transposon comprising the following DNA sequences:

```
Sleeping Beauty 5' ITR:
CAGTTGAAGTCGGAAGTTTACATACACTTAAGTTGGAGTCATTAAAAC

TCGTTTTTCAACTACTCCACAAATTTCTTGTTAACAAACAATAGTTTT

GGCAAGTCAGTTAGGACATCTACTTTGTGCATGACACAAGTCATTTTT

CCAACAATTGTTTACAGACAGATTATTTCACTTATAATTCACTGTATC

ACAATTCCAGTGGGTCAGAAGTTTACATACACTAAGT

Sleeping Beauty 3' ITR:
ATTGAGTGTATGTAAACTTCTGACCCACTGGGAATGTGATGAAAGAAA

TAAAAGCTGAAATGAATCATTCTCTCTACTATTATTCTGATATTTCAC

ATTCTTAAAATAAAGTGGTGATCCTAACTGACCTAAGACAGGGAATTT

TTACTAGGATTAAATGTCAGGAATTGTGAAAAAGTGAGTTTAAATGTA

TTTGGCTAAGGTGTATGTAAACTTCCGACTTCAACTG

PiggyBac 5' ITR:
<u>CCCTAGAAAGATAGTCTGCGTAAAATTGACGCATG</u>CATTCTTGAAATA

TTGCTCTCTCTTTCTAAATAGCGCGAATCCGTCGCTGTGCATTTAGGA

CATCTCAGTCGCCGCTTGGAGCTCCCGTGAGGCGTGCTTGTCAATGCG

GTAAGTGTCACTGATTTTGAACTATAACGACCGCGTGAGTCAAAATGA

CGCATGATTATCTTTTACGTGACTTTTAAGATTTAACTCATACGATAA

TTATATTGTTATTTCATGTTCTACTTACGTGATAACTTATTATATATA

TATTTTCTTGTTATAGATATC
(minimal sequence is underlined and bold, i.e.,
first 35 bp)

PiggyBac 3' ITR:
TAAAAGTTTTGTTACTTTATAGAAGAAATTTTGAGTTTTTGTTTTTTT

TTAATAAATAAATAAACATAAATAAATTGTTTGTTGAATTTATTATTA

GTATGTAAGTGTAAATATAATAAAACTTAATATCTATTCAAATTAATA

AATAAACCTCGATATACAGACCGATAAAACA**<u>CATGCGTCAATTTTACG</u>**

<u>CATGATTATCTTTAACGTACGTCACAATATGATTATCTTTCTAGGG</u>
(minimal sequence is underlined and bold, i.e.,
first 35 bp)
```

In some embodiments, the only transposon fragment in the transplanted haplotype consists of a PiggyBac 5' ITR and a PiggyBac 3' ITR. In some embodiments, the only transposon fragment in the transplanted haplotype consists of a Sleeping Beauty 5' ITR and a Sleeping Beauty 3' ITR. In some embodiments, the transplanted haplotype comprises a transgene flanked by a PiggyBac 5' ITR and a PiggyBac 3' ITR. In some embodiments, the transplanted haplotype comprises a transgene flanked by a Sleeping Beauty 5' ITR and a Sleeping Beauty 3' ITR. In some embodiments, the transplanted haplotype comprises a transgene flanked by the following sequences: 5' CCCTAGAAAGATAGTCTGCGTAAAAT-TGACGCATG and on the 3' end (from 5' to 3'): CATGCGT-CAATTTTACGCATGATTATCTTTAACG-TACGTCACAATATGATTATC TTTCTAGGG. In some embodiments, the transplanted haplotype comprises a hyperactive transposon.

The present invention also provides a composition that comprises a cell culture medium, glial cell-derived neurotrophic factor (GDNF), Fibroblast Growth Factor-2 (FGF2), and B27-minus vitamin A supplement solution. In some embodiments, the composition further comprises any one or more of Ham's F12 nutrient mixture, 2-mercaptoethanol, and L-glutamine. In some embodiments, the cell culture medium is Dulbecco's Modified Eagle Medium (DMEM). In addition, 2-mercaptoethanol and L-glutamine can be substituted by similar functioning compounds well known to the skilled artisan.

In some embodiments, the composition described above can comprise from about 10 ng/ml to about 30 ng/ml GDNF, from about 10 ng/ml to about 30 ng/ml FGF2, and about a 1× concentration of B27-minus vitamin A supplement solution. In some embodiments, the composition can comprise a 1:1 ratio of cell culture medium, such as DMEM, to Ham's F12 nutrient mixture. The composition can also comprise from about 50 to about 120 µM 2-mercaptoethanol, and from about 3 to about 10 mM L-glutamine.

In some embodiments, the composition described above can comprise a 1:1 ratio of DMEM to Ham's F12 nutrient mixture, 20 ng/ml GDNF, 25 ng/ml FGF2, 100 µM 2-mercaptoethanol, 6 mM L-glutamine, and a 1× concentration of B27-minus vitamin A supplement solution. In some embodiments, the composition described above can comprise a 1:1 ratio of DMEM to Ham's F12 nutrient mixture, about 20 ng/ml GDNF, about 25 ng/ml FGF2, about 100 µM 2-mercaptoethanol, about 6 mM L-glutamine, and a 1× concentration of B27-minus vitamin A supplement solution.

The present invention also provides a male rat of a predetermined genetic background comprising a transplanted haplotype derived from a rat spermatogonial stem cell line, wherein the rat is sterile absent the presence of the transplanted haplotype. In some embodiments, the male rat is DAZL-deficient. In some embodiments, the male rat expresses a small hairpin RNA transgene that degrades DAZL mRNA. In some embodiments, the predetermined genetic background is Sprague Dawley or Fisher 344. In some embodiments, the transplanted haplotype comprises an internal tandem repeat (ITR) from a transposon. In some embodiments, the transplanted haplotype comprises an ITR from a transposon selected from the piggyBac ITR, Sleeping Beauty ITR, or a combination thereof.

The present invention also provides a rat spermatogonial stem cell line of a predetermined genetic background. In some embodiments, the predetermined genetic background of the rat spermatogonial stem cell line is Sprague-Dawley. In some embodiments, the predetermined genetic background of the rat spermatogonial stem cell line is Sprague-Fisher 344. In some embodiments, the transplanted haplotype of the rat spermatogonial stem cell line comprises an internal tandem repeat (ITR) from a transposon. The ITR consists of a 5' sequence and a 3' sequence flanking a gene of interest. In some embodiments, the transplanted haplotype of the rat spermatogonial stem cell line comprises at least one ITR from a transposon selected from the piggyBac ITR, Sleeping Beauty ITR, Tol2 ITR, Frog Prince ITR or a combination thereof. In some embodiments, the rat spermatogonial stem cell line can be cultured from about 150 days to about 205 days. In some embodiments, the rat spermatogonial stem cell line has a doubling time of about 8 or 9 days. In some embodiments, the rat spermatogonial stem cell line has a doubling time of no less than 8.4 days. In some embodiments, the rat spermatogonial stem cell line has a doubling time of about 8.4 days. In some embodiments, the rat spermatogonial stem cell line expands no less than about 20,000 times as compared to the number of cells seeded in culture. In some embodiments, the rat spermatogonial stem cell line expands no less than about 2,000,000 times as compared to the number of cells seeded in culture. In some embodiments, the rat spermatogonial stem cell line expands no less than about 30,000 times as compared to the number of cells seeded in culture. In some embodiments, the rat spermatogonial stem cell line expands no less than about 50,000 times as compared to the number of cells seeded in culture. In some embodiments, the rat spermatogonial stem cell line expands no less than about 80,000 times as compared to the number of cells seeded in culture. In some embodiments, the rat spermatogonial stem cell line expands no less than about 100,000 times as compared to the number of cells seeded in culture. In some embodiments, the rat spermatogonial stem cell line expands no less than about 200,000 times as compared to the number of cells seeded in culture. In some embodiments, the rat spermatogonial stem cell line expands no less than about 300,000 times as compared to the number of cells seeded in culture. In some embodiments, the rat spermatogonial stem cell line expands no less than about 300,000 times as compared to the number of cells seeded in culture. In some embodiments, the rat spermatogonial stem cell line expands no less than about 400,000 times as compared to the number of cells seeded in culture. In some embodiments, the rat spermatogonial stem cell line expands no less than about 500,000 times as compared to the number of cells seeded in culture. In some embodiments, the rat spermatogonial stem cell line expands no less than about 600,000 times as compared to the number of cells seeded in culture. In some embodiments, the rat spermatogonial stem cell line expands no less than about 700,000 times as compared to the number of cells seeded in culture. In some embodiments, the rat spermatogonial stem cell line expands no less than about 900,000 times as compared to the number of cells seeded in culture. In some embodiments, the rat spermatogonial stem cell line expands no less than about 1,000,000 times as compared to the number of cells seeded in culture.

In some embodiments, the rat spermatogonial stem cell line expands no less than about 1,500,000 times as compared to the number of cells seeded in culture. In some embodiments, the rat spermatogonial stem cell line expands about 2,0000,000 times as compared to the number of cells seeded in culture.

In some embodiments, the rat spermatogonial stem cell line can be frozen at about −196 degrees Celsius and possess at least 20%, 30%, 40%, 50%, 60%, 70%, 80%, 90%, or 95% cell viability upon thawing and subsequent culturing.

The present invention also comprises composition that comprises a spermatogonial stem cell of a predetermined background and culture medium. In some embodiments, the culture medium comprises glial cell-derived neurotrophic factor (GDNF), Fibroblast Growth Factor-2 (FGF2), and B27-minus vitamin A supplement solution. In some embodiments, the composition further comprises any one or more of Ham's F12 nutrient mixture, 2-mercaptoethanol, and L-glutamine. In some embodiments, the cell culture medium is Dulbecco's Modified Eagle Medium (DMEM). In addition, 2-mercaptoethanol and L-glutamine can be substituted by similar functioning compounds well known to the skilled artisan. In some embodiments, the composition can comprise from about 10 ng/ml to about 30 ng/ml GDNF, from about 10 ng/ml to about 30 ng/ml FGF2, and about a 1× concentration of B27-minus vitamin A supplement solution. In some embodiments, the composition can comprise a 1:1 ratio of cell culture medium, such as DMEM, to Ham's F12 nutrient mixture. The composition can also comprise from about 50 to about 120 µM 2-mercaptoethanol, and from about 3 to about 10 mM L-glutamine. The composition supports in vitro culturing of spermatogonial stem cells. The spermatogonial stem cell of a predetermined background can comprise any or all of the features described herein for a spermatogonial stem cell. In some embodiments, the composition can comprise about 20 ng/ml GDNF, about 20 ng/ml FGF2, and about a 1× concentration of B27-minus vitamin A supplement solution. In some embodiments, the composition can comprise a 1:1 ratio of cell culture medium, such as DMEM, to Ham's F12 nutrient mixture.

The present invention also provides a method of introducing a mutation or transgene of interest into the genome of a male rat of a predetermined genetic background, wherein said rat is sterile absent the presence of a transplanted haplotype comprising the steps of: (a) culturing an isolated rat spermatogonial stem cell line of a predetermined genetic background; and (b) transplanting the rat spermatogonial stem cell line of a predetermined genetic background into the testes of the male rat, wherein the haplotype comprises a transposon sequence or a fragment thereof.

The present invention also provides a method of introducing a transgene or mutated gene of interest into the genome of a male rat of a predetermined genetic background, wherein said rat is sterile absent the presence of a transplanted haplotype comprising:

(a) providing a rat spermatogonial stem cell line of a predetermined genetic background; (b) genetically modifying the rat stem cell line with a transposon; and (c) transplanting the rat spermatogonial stem cell line of a predetermined genetic background into the testes of the male rat.

In some embodiments, the transplanted haplotype comprises an internal tandem repeat (ITR) from a transposon. In some embodiments, the transplanted haplotype comprises an ITR from a transposon selected from the piggyBac ITR, Sleeping Beauty ITR, or a combination thereof. In some embodiments, the transplanted haplotype comprises a fragment of a transposon sequence comprising the following two sequences: CCCTAGAAAGATAGTCTGCGTAAAAT-TGACGCATG and CATGCGTCAATTTTACGCATGAT-TATCTTTAACGTACGTCACAATATGATTATC
TTTCTAGGG. In some embodiments, the transplanted haplotype comprises at least two noncontiguous fragments of a transposon sequence comprising the following two sequences:

CCCTAGAAAGATAGTCTGCGTAAAATTGACGCATGCATTCTTGAAATATT

GCTCTCTCTTTCTAAATAGCGCGAATCCGTCGCTGTGCATTTAGGACATC

TCAGTCGCCGCTTGGAGCTCCCGTGAGGCGTGCTTGTCAATGCGGTAAGT

GTCACTGATTTTGAACTATAACGACCGCGTGAGTCAAAATGACGCATGAT

TATCTTTTACGTGACTTTTAAGATTTAACTCATACGATAATTATATTGTT

ATTTCATGTTCTACTTACGTGATAACTTATTATATATATTTTCTTGTT

ATAGATATC
and

TAAAAGTTTTGTTACTTTATAGAAGAAATTTTGAGTTTTTGTTTTTTTT

AATAAATAAATAAACATAAATAAATTGTTTGTTGAATTTATTATTAGTAT

GTAAGTGTAAATATAATAAAACTTAATATCTATTCAAATTAATAAATAAA

CCTCGATATACAGACCGATAAAACACATGCGTCAATTTTACGCATGATTA

TCTTTAACGTACGTCACAATATGATTATCTTTCTAGGG.

In some embodiments, wherein the transplanted haplotype comprises a fragment of a transposon sequence consisting of the PiggyBac 5' ITR and the PiggyBac 3' ITR. In some embodiments, the transplanted haplotype comprises a fragment of a transposon sequence consisting of the Sleeping Beauty 5' ITR and the Sleeping Beauty 3' ITR.

Those having ordinary skill in the art can readily design and produce mutations in the DNA sequences above having substantially identical nucleotide sequences of transposons or transposon ITR with deletions and/or insertions and/or conservative substitutions of nucleotide base pairs. Such substitutions are well-known and are based the secondary structure and free energy of the DNA sequence and structural characteristics of each nucleotide base. Derivatives include fragments of transposons with deletions and/or insertions and/or conservative substitutions. In some embodiments, the transplanted haplotype comprises a fragment of a transposon sequence consisting of a DNA sequence that is 90% homologous to the PiggyBac 5' ITR and a DNA sequence that is 90% homologous the PiggyBac 3' ITR. In some embodiments, the transplanted haplotype comprises a fragment of a transposon sequence consisting of a DNA sequence that is 95% homologous to the PiggyBac 5' ITR and a DNA sequence that is 95% homologous the PiggyBac 3' ITR. In some embodiments, the transplanted haplotype comprises a fragment of a transposon sequence consisting of a DNA sequence that is 98% homologous to the PiggyBac 5' ITR and a DNA sequence that is 98% homologous the PiggyBac 3' ITR. In some embodiments, the transplanted haplotype comprises a fragment of a transposon sequence consisting of a DNA sequence that is 99% homologous to the Sleeping Beauty 5' ITR and a DNA sequence that is 99% homologous the Sleeping Beauty 3' ITR. In some embodiments, the transplanted haplotype comprises a fragment of a transposon sequence consisting of a DNA sequence that is 90% homologous to the Sleeping Beauty 5' ITR and a DNA sequence that is 90% homologous the Sleeping Beauty 3' ITR. In some embodiments, the transplanted haplotype comprises a fragment of a transposon sequence consisting of a DNA sequence that is 95% homologous to the Sleeping Beauty 5' ITR and a DNA sequence that is 95% homologous the Sleeping Beauty 3' ITR. In some embodiments, the transplanted haplotype comprises a fragment of a transposon sequence consisting of a DNA sequence that is 98% homologous to the Sleeping Beauty 5' ITR and a DNA sequence that is 98% homologous the Sleeping Beauty 3' ITR. In some embodiments, the transplanted haplotype comprises a fragment of a transposon sequence consisting of a DNA sequence that is 99% homologous to the Sleeping Beauty 5' ITR and a DNA sequence that is 99% homologous the Sleeping Beauty 3' ITR.

In some embodiments, the transplanted haplotype comprises a fragment of a transposon sequence comprising a DNA sequence that is 90% homologous to the PiggyBac 5' ITR and a DNA sequence that is 90% homologous the PiggyBac 3' ITR. In some embodiments, the transplanted haplotype comprises a fragment of a transposon sequence comprising a DNA sequence that is 95% homologous to the PiggyBac 5' ITR and a DNA sequence that is 95% homologous the PiggyBac 3' ITR. In some embodiments, the transplanted haplotype comprises a fragment of a transposon sequence comprising a DNA sequence that is 98% homologous to the PiggyBac 5' ITR and a DNA sequence that is 98% homologous the PiggyBac 3' ITR. In some embodiments, the transplanted haplotype comprises a fragment of a transposon sequence comprising a DNA sequence that is 99% homologous to the Sleeping Beauty 5' ITR and a DNA sequence that is 99% homologous the Sleeping Beauty 3' ITR. In some embodiments, the transplanted haplotype comprises a fragment of a transposon sequence comprising a DNA sequence that is 90% homologous to the Sleeping Beauty 5' ITR and a DNA sequence that is 90% homologous the Sleeping Beauty 3' ITR. In some embodiments, the transplanted haplotype comprises a fragment of a transposon sequence comprising a DNA sequence that is 95% homologous to the Sleeping Beauty 5' ITR and a DNA sequence that is 95% homologous the Sleeping Beauty 3' ITR. In some embodiments, the transplanted haplotype comprises a fragment of a transposon sequence comprising a DNA sequence that is 98% homologous to the Sleeping Beauty 5' ITR and a DNA sequence that is 98% homologous the Sleeping Beauty 3' ITR. In some embodiments, the transplanted haplotype comprises a fragment of a transposon sequence comprising a DNA sequence that is 99% homologous to the Sleeping Beauty 5' ITR and a DNA sequence that is 99% homologous the Sleeping Beauty 3' ITR.

In some embodiments, the male rat of the composition and method claims is transplanted via injection of the cells. In some embodiments, the male rat is DAZL-deficient. In some embodiments, the male rat expresses a small hairpin RNA transgene that degrades DAZL mRNA. In some embodiments, the predetermined genetic background is Sprague Dawley or Fisher 344. In some embodiments, the predetermined genetic background is an outbred strain of rat. In some embodiments, the predetermined genetic background is an inbred strain of rat. In some embodiments, the transplanted stem cell line comprises an internal tandem repeat (ITR) from a transposon. In some embodiments, the transplanted stem cell line comprises an ITR from a transposon selected from the piggyBac ITR, Sleeping Beauty ITR, or a combination thereof. In some embodiments, the male rat of a predetermined genetic background comprises a transgene or mutation. In some embodiments, the male rat of a predetermined genetic background comprises a transposon. In some embodiments, the male rat of a predetermined genetic background comprises a transposon ITR. In some embodiments, the rat spermatogonial stem cell line comprises at least one ITR from a transposon selected from the piggyBac ITR, Sleeping Beauty ITR, Tol2 ITR, Frog Prince ITR or a combination thereof. In some embodiments, the male rat of a predetermined genetic background at least one ITR from a transposon selected from the piggyBac ITR, Sleeping Beauty ITR, Tol2 ITR, Frog Prince ITR or a combination thereof.

The present invention is further described by reference to the following examples, which are illustrative only and not limiting of the invention.

Example 1

Generation of DAZL-Deficient Rats on a Fischer F344 Genetic Background

Male DAZL-deficient rats are sterile, whereas female DAZL-deficient rats remain fully fertile. Somatic testis cells in DAZL-deficient rats are able to support full development of spermatozoa from healthy donor spermatogonial stem cell lines derived from normal Sprague Dawley rats, thus the effects of DAZL on disrupting sperm cell development are restricted to the germ-line. Importantly, the absence of endogenous sperm production by DAZL-deficient rats allows the sperm produced from the transplanted, donor spermatogonial stem cell lines to develop and function within an environment devoid of any competition from the hosts germline. The selected, genetically modified haploid gametes can then be used to produce mutant rats through natural mating of recipients, or by assisted reproduction techniques.

To use the DAZL-deficient recipient rat model as a strategy to enrich for fully functional Fischer F344 Rat spermatogonial stem cell lines that can develop into fertilization competent gametes, DAZL-deficient rats of a predominantly Fischer F344 genetic background were first generated to avoid immuno-compatibility barriers that exist between the Sprague Dawley and Fischer F344 rat lines. Because initial existing strains of DAZL-deficient rats were on a Sprague Dawley rat genetic background, female DAZL-deficient rats were first bred with pure male Fischer F344 rats (Harlan, Inc). Based on Mendelian inheritance of maternal and paternal genes, the progeny (F1 progeny) produced from this cross yielded rats that consisted of ~half Fischer F344 and ~half Sprague Dawley genetic background. Accordingly, ~50% of Female F1 progeny from this first out-cross are also DAZL-deficient due to inheritance of the DAZL-shRNA transgene. DAZL-deficient F1 female rats were then back-crossed with pure, male Fischer F344 rats (Harlan, Inc) again to enrich for the Fischer F344 genetic background by ~75% in the F2 progeny. At this point, F2 DAZL-deficient males and females should be enriched for Fischer F344 immuno-compatibility factors by at least 50-75%. DAZL-deficient F2 males of this hybrid background can now serve as recipients for pure donor Fischer F344 rat spermatogonial stem cell lines. Also, the F2 females generated can be used to further enrich for the Fischer F344 immuno-compatibility factors in DAZL-deficient rats by additional back-crossing with pure, male Fischer F344 rats (Harlan, Inc) until near genetic homogeneity with the derived Fischer F344 rat spermatogonial lines. The number of back-crosses to achieve optimal spermatozoon development from donor Fischer F344 spermatogonial stem cell lines is not currently known, but could be maximal after the initial cross.

Example 2

Nutrient Mixture for Culturing Rat Spermatogonial Stem Cells

SG medium is an effective and efficient nutrient mixture for growing rat spermatogonial stem cells. SG medium is composed of Dulbecco modified Eagle medium:Ham F12 nutrient mixture (1:1), 20 ng/ml GDNF, 25 ng/ml FGF2, 100 µM 2-mercaptoethanol, 6 mM L-glutamine and a 1× concentration of the B27-Minus Vitamin-A Supplement solution. With the use of SG medium, six spermatogonial lines were derived from the testes of six, separate Sprague Dawley rats. After proliferating over a 120 day period in SG medium, stem cells within the spermatogonial cultures effectively regenerated spermatogenesis in testes of busulfan-treated recipient rats, which transmitted the donor cell haplotype to greater than 75% of progeny by natural breeding. Sub-culturing in SG medium did not require protease treatment, and was achieved by passaging the loosely bound spermatogonial cultures at 1:3 dilutions onto fresh mono-layers of irradiated, DR4 mouse fibroblasts every 12 days. Spermatogonial lines derived and propagated using SG medium were characterized as homogenous populations of ZBTB $16^+$, $DAZL^+$ cells endowed with spermatogonial stem cell potential.

Materials

Dispase, rat-tail collagen I-coated culture dishes and gelatin-coated culture dishes were from, Fisher, Inc. Phosphate buffered saline (PBS), nonessential amino acids, Minimum Essential Medium (MEM) vitamin solution, 1-glutamine solution, trypsin-EDTA solutions (0.05% wt/vol trypsin with 0.2 gaiter EDTA.4Na; or 0.25% wt/vol trypsin with 0.38 g/liter EDTA.4Na), antibiotic-antimycotic solution (catalogue 15240-062), Hoechst 33342 and AlexaFlour-594-conjugated, goat-anti-rabbit and goat-anti-mouse IgGs were from Invitrogen. Bovine serum albumin (BSA) and dimethyl-sulfoxide (DMSO) were from Calbiochem. Fetal bovine serum (FBS) for mouse embryonic fibroblast (MEF) medium was from Hyclone (catalogue SH30071.03). Blocking reagent was from Roche Applied Biosciences. Mouse laminin, sodium bicarbonate, trypan blue, Dulbecco's Modified Eagle's Medium (DMEM, Cat#D5648), and DMEM:Ham's F12 (1:1) Nutrient Mixture (DMEM:Ham's F12, Cat#D8437) were from Sigma. See Sigma Cat#D5648 and D8437 Product Information Sheet.

Animal Care and Use

Protocols for the use of rats in this study were approved by the Institutional Animal Care and Use Committee (IACUC) at UT-Southwestern Medical Center in Dallas. Rats used for this study were housed in individually ventilated, Lab Products 2100 cages in a dedicated room with atmosphere controls set to 72° F., 45-50% humidity during a 12 hour light/dark (i.e. Light cycle=6:00 am-6:00 pm, Central Standard Time adjusted for daylight savings time). Rats were fed Harlan Teklad Irradiated 7912, LM-485 Mouse/Rat Diet, 5% fat Diet and a continuous supply of reverse osmosis water.

Isolating Enriched Fractions of Undifferentiated Spermatogonia

Seminiferous tubules were isolated from testes of 23-24 day old WT Sprague Dawley (SD) rats (Hsd:Sprague Dawley SD, Harlan, Inc.) or homozygous SD-Tg(Gt(ROSA)26Sor-EGFP)2-4Reh transgenic rats. Rats of the SD-Tg(Gt(ROSA)26Sor-EGFP)2-4Reh line were produced by pronuclear injection and are referred to as GCS-EGFP rats because they exhibit germ cell specific (GCS) expression of enhanced green fluorescent protein (EGFP). The tubules were enzymatically and mechanically dissociated into a cellular suspension to generate cultures of testis cells in serum-containing medium, as described, except that a medium volume of 10 ml/rat was applied for all centrifugation and filtration steps. The testis cell cultures were then used to isolate enriched populations of laminin-binding spermatogonia following previously established methods, which describe how to first remove >95% of somatic testis cells from the germ cell population by negative selection on plastic and collagen, before positive selection for the spermatogonial stem cells based on their ability to bind to laminin. By this procedure, the freshly isolated laminin-binding germ cell population contains >90% undifferentiated, type A spermatogonia (ZBTB16$^+$, DAZL$^+$) in the single (~88%) or paired (~12%) cell state. Also, it should be noted that fractions of laminin-binding spermatogonia isolated by this procedure contain ~4% somatic cells, and ~5% differentiating spermatogonia plus spermatocytes. In this study, a single rat of this age range yielded $3.62 \times 10^5 \pm 0.93 \times 10^5$ (SD, n=6 rats) laminin-binding spermatogonia, as compared to yields reported for this procedure when scaled for processing pools of testes from multiple rats at 22-24 days of age (i.e., $1.98 \times 10^5 \pm 0.56 \times 10^5$ cells/rat, SD, n=34 primary cultures).

Derivation of Spermatogonial Lines

To derive rat spermatogonial stem cell lines, freshly isolated laminin-binding spermatogonia from individual rats were plated separately into gelatin-coated wells (3.5 cm) of a culture plate at ~$1.9 \times 10^4$ cells/cm$^2$ in 0.37 ml/cm$^2$ of Spermatogonial Medium (SG Medium). Components of SG Medium are presented in Table 2 and Table 3. As reported for this procedure using SA Medium, which lacks both serum and vitamin-A, spermatogonia cultured on gelatin using SG Medium were observed loosely bound to the culture plate, bound to residual adherent somatic testis cells, and in suspension; many of the spermatogonia in suspension adhered to each other as cellular "clusters" of variable size. In contrast, the small fraction of contaminating somatic testis cells attached avidly and spread out on the gelatin matrix. After an initial selection for 40-48 hours on the gelatin-coated plates, spermatogonia in suspension (i.e., including loosely bound spermatogonia), were harvested free from the contaminating somatic testis cells by pipetting. Harvested spermatogonia were pelleted at 200×g for 4 minutes, the supernatant was discarded and the cellular pellet was suspended in SG Medium and plated into fresh gelatin-coated wells (3.5 cm) for an additional 72-96 hours. After this point (i.e., after depletion of essentially all somatic testis cells), suspensions of spermatogonia from each rat that survived through the final selection steps on gelatin were harvested into fresh SG Medium and passaged into 2.2 cm culture wells (i.e., 12-well culture dish) containing feeder layers of irradiated mouse embryonic fibroblasts (MEFs) Methods for preparing MEF feeder layers are described below. The initial passage of spermatogonial cultures after their plating onto MEF feeder layers required a 1:1 to 1:2 split into the same size wells at 14-21 days after their initial seeding onto the MEFs. In this situation, because irradiated MEF feeder layers are not as effective after 14 days in culture, fresh MEFs ($2 \times 10^4$/cm$^2$) were "spiked" into the on-going spermatogonial cultures on day 12-14 so as to by-pass the need to passage the spermatogonia before expanding to larger numbers. However, once established by the second or third passage on MEFs, cultures of spermatogonia were passaged at ~1:3 dilutions onto a fresh monolayer of MEFs every 10-14 days at ~$3 \times 10^4$ cells/cm$^2$ for over 5 months (~12 passages). For passaging, cultures were first harvested by gently pipetting them free from the MEFs. After harvesting, the "clusters" of spermatogonia were dissociated by gentle trituration with 20-30 strokes through a p1000 pipet in their SG culture medium. The dissociated cells were pelleted at 200×g for 4 minutes and the number of cells recovered during each passage was determined by counting them on a Hemocytometer (Note: spermatogonial clusters were not disrupted for counting until the second passage on MEFs). As verified by expression of the GCS-EGFP marker transgene, spermatogonia were easily distinguished during counting as the predominant population of smaller, round cells with smooth surfaces, as compared to occasionally observed, larger and often irregular shaped irradiated MEFs. All culture steps for deriving and propagating spermatogonial lines when in SG Medium were performed at 37° C./5% CO$_2$. The doubling time for the number of GCS-EGFP$^+$ cells that could be harvested from cultures of each spermatogonial line after subsequent passages between days 30 and 150 in culture on MEFs were calculated by non-linier regression analysis using the least squares fit model set for automatic outlier exclusion provided as the Exponential Growth Equation in the GraphPad Prism program (Version 5.01, GraphPad Software, Inc.).

Preparation of Fibroblast Feeder Layers

Primary stocks of DR4MEFs were purchased from ATCC, Inc., and expanded in DMEM supplemented 1.5 g/l sodium bicarbonate, 15% heat-inactivated FBS (MEF medium) at 37° C./5% CO$_2$ for up to 4 passages following their thawing and initial plating (i.e. passage 0) from the vial received from the manufacturer. Following expansion to passages 3 and 4, secondary stocks of MEFs were irradiated (120 Gy) and then cryo-preserved in liquid nitrogen for future use by the manufacturer's protocol. Prior to use for culture with spermatogonia, the MEFs were thawed and plated into gelatin-coated dishes ($4.5 \times 10^4$ cells/cm$^2$) in MEF medium for 16-48 hr, rinsed 1× with PBS and then pre-incubated in SG Medium for an additional 16-48 hr. The SG Medium used for pre-incubation was then discarded and spermatogonia were passaged onto the MEFs in fresh SG Medium.

Germ Cell Transplantation and Progeny Genotyping

WT Sprague Dawley rats at 12 days of age were injected (i.p.) with 12.5 mg/kg busulfan (4 mg/ml in 50% DMSO) and then used as recipient males at 24 days of age. Busulfan is a spermatogonial toxin commonly used to kill spermatogonia in recipient rat testes prior to transplantation because it increases the colonization efficiency by the donor stem cells. Donor cells were loaded into injection needles fashioned from 100 µl glass capillary tubes at a concentration of $3 \times 10^5$ cells/65 µl SG Medium containing 0.04% (wt/vol) trypan blue and then the entire volume was transplanted into the seminiferous tubules of anesthetized rats by retrograde injection through the rete testes. Recipient males transplanted with GCS-EGFP spermatogonia were paired with wild-type female Sprague Dawley of similar age at 75 days post transplantation. Transgenic rat progeny from wild-type recipients and wild-type females were determined by qtPCR analysis of genomic DNA using primers specific to the GCS-EGFP transgene and the 18S ribosomal subunit; relative transgene copy number in F2 progeny from hemizygous crosses were verified by Southern dot blot hybridization analysis of the genomic DNA using a probe specific for the GCS-EGFP transgene. Genotyping results were also confirmed in representative progeny by direct visualization of transgene expression in testes and ovaries using a Nikon SMZ 1500 fluorescence stereomicroscope.

Immunocytochemistry

Cultures of germ cells (2 cm$^2$) were washed twice with DMEM:Ham's F12 medium (0.6 ml/well) and then fixed for 7.5 mM with 4% paraformaldehyde, 0.1M sodium phosphate, pH 7.2 (0.4 ml/well). After fixation the cells were washed 3 times with PBS (0.6 ml/well) and then incubated for 15 min in PBS containing 0.1% (v/v) triton-X 100 (0.4 ml/well). The cells were then washed 3 times in PBS (0.6 ml/well) and non-specific, protein-binding sites were blocked by incubating the cells in 0.1% w/v blocking reagent (0.4 ml/well, Roche, Inc.) for 1.5 hr at 22-24° C. The blocking reagent was then removed and the cells were incubated for 16 hr at 22-24° C. in primary antibodies (0.4 ml/well). The mouse, anti-human ZBTB 16 IgG (Calbiochem, Inc.) and the purified non-immune mouse IGHG1 (Santa Cruz, Inc) fractions were each diluted to 1 µl/ml in blocking reagent. The anti-DAZL-3 IgG and the preimmune-3 IgG fractions were diluted to 250 ng/ml in blocking reagent. Following incubation in primary antibodies, the cells were washed 3 times for 5 min with 0.6 ml/well 10 mM Tris-HCl, 150 mM NaCl, 0.1% Tween-20, pH 7.5 (TBST) to remove unbound IgG. The cells were then incubated for 40 min at 22-24° C. in conjugated, secondary antibody (0.4 ml/well) diluted to 4 µg/ml in PBS containing 5 µg/ml Hoechst 33342 dye. Following incubation in secondary antibodies, the cells were washed 3 times for 5 min with TBST (0.6 ml/well) to remove unbound IgG and dye prior to viewing in fresh PBS (0.4 ml/well) using an inverted Olympus IX70 microscope (Olympus, Inc.).

Formula and Effects of a New Spermatogonial Culture Medium:

A DMEM:Hams-F12 nutrient mixture supplemented with GDNF, bFGF, B-27-Minus Vitamin-A, L-glutamine and 2-mercaptoethanol was found to support the continued propagation (>2 million-fold expansion in cell number) of a previously established rat spermatogonial line on MEFs following its initial derivation, propagation and cryo-preservation in SA medium. The newly formulated spermatogonial medium was termed SG medium, and further eliminated the need to add MEM-vitamins, estradiol, pyruvate, lactate, ascorbate, non-essential amino acids, glucose and StemPro supplement. The SG medium was also used at a 100% success rate to derive new proliferating spermatogonial lines from individual wild-type (n=3) and homozygous GCS-EGFP transgenic rats (n=3) on a Sprague Dawley background by our previously established methods (See Hamra et al., Proc Natl Acad Sci USA 2005; 102:17430-17435), but without the need to further enrich the starting spermatogonial population by flow cytometry or magnetic cell sorting techniques. The proliferating germlines derived in SG medium were characterized as undifferentiated spermatogonia based on co-expression of the marker proteins, PLZF and DAZL, and their ability to effectively colonize the seminiferous tubules of busulfan-treated rats. The lines were sub-cultured in SG medium by pipetting, and did not require protease treatment. The newly derived lines displayed doubling times of 8.4±0.2 days (mean±SD, n=4) when exponential growth curves were fit between culture days 30 and 150 after their initial seeding onto MEFs in SG medium as freshly isolated laminin-binding spermatogonia. For comparison, spermatogonial lines derived and propagated in SA medium displayed doubling times of 6.5±1.8 days (mean±SD, n=4) when analyzed between culture days 30 and 150 after their initial seeding onto MEFs.

To determine the spermatogenic potential of the new rat spermatogonial lines (RSGL) that were derived using SG medium, RSGL-GCS9 and RSGL-GCS10 from GCS-EGFP rats were propagated for 111 and 120 days in culture, respectively, over a total of 9 to 10 passages prior to being transplanted into testes of busulfan-treated, wildtype rats at ~$3 \times 10^5$ cells/testis (i.e. after expanding in cell number by >20.000-fold after their initial seeding onto MEFs). When the recipients of RSGL-GCS9 and RSGL-GCS10 were paired with wild-type females at 75 days post-transplantation, they yielded 78.9±10.4% and 67.2±16.4% germline transmission, respectively, from spermatozoa produced by the donor stem cells (GCS9 recipients: mean±SD, n=19 litters, 193 total pups; GCS10 recipients: mean±SD, n=9 litters, 107 total pups). Germline transmission of the donor cell haplotype was based on inheritance of the GCS-EGFP transgene by F1 progeny. Resulting non-Mendelian ratios (i.e. <100% transgenic F1 progeny) were due to competition from residual wildtype spermatozoa produced by the recipients. However, transmission of the GCS-EGFP transgene to F2 progeny from crosses between hemizygous F1 cousins did yield Mendelian ratios (wildtype=21%, hemizygous=51%, homozygous=28%; n=3 litters, 47 total pups).

Testes from recipients transplanted with RSGL-GCS9 and RSGL-GCS10 were next analyzed histologically for long-term, spermatogenesis colony forming potential. When evaluated at 206-263 days following transplantation, 92.5±2.4% (mean±SEM, n=4) and 81.5±9.5% (mean±SEM, n=3) of seminiferous tubule cross sections that were colonized by RSGL-GCS9 and RSGL-GCS10, respectively, showed development of EGFP+ spermatogonia to the elongating spermatid stage. Thus, spermatogonial lines derived in SG medium were classified as essentially pure cultures of undifferentiated spermatogonia containing fully functional sperm stem cells.

Example 3

Deriving Spermatogonial Lines from Inbred Fischer, F344 NHsd Rats

Total laminin-binding (LB) spermatogonia ($2.3 \times 10^6$) were isolated from the seminiferous tubules of 10 inbred Fischer Rats (F344 NHsd Rats, Harlan, Inc) at 22 days of age. The isolated spermatogonia were then used to derive lines of proliferating spermatogonia in Spermatogonial Culture Medium (SG Medium) using established methods. In brief, following isolation, LB spermatogonia were plated equally into 6, gelatin-coated wells (9.6 cm$^2$ wells) of a 6-well culture plate. The cells were harvested by gentle pipetting, pelleted at 200×g for 4 min, suspended in fresh SG Medium and then passed 3 times sequentially at a 1:1 ratio onto fresh gelatin-coated wells for 44-48 hr incubation periods between passages over a total of 6 days. Starting on the 7$^{th}$ day, cells were harvested from all wells as described above, pooled together and plated into 1, 9.6 cm$^2$ well of mouse embryonic fibroblasts (MEFs) and then maintained and propagated in SG Medium on MEFs as previously reported.

Alternatively, 1.2×10$^6$ total LB spermatogonia were isolated from the seminiferous tubules of 10 inbred Fischer Rats (F344 NHsd Rats, Harlan, Inc) at 18 days of age, as described above, but with the following modifications. In brief, following their isolation, LB spermatogonia were plated equally into 4, gelatin-coated wells (9.6 cm$^2$ wells) of a 6-well culture plate. The cells were harvested by gentle pipetting, pelleted at 200×g for 4 min and passed two times sequentially into fresh SG Medium at a 1:1 ratio onto fresh gelatin-coated wells for 22-24 hr incubation periods between passages over a total of 2 days. Starting on the 3$^{rd}$ day, cells were harvested from all wells as described above, pooled together and plated into 1, 9.6 cm$^2$ well of MEFs in SG Medium for 7 days. The spermatogonia were harvested from off the MEFs by pipetting as described above and incubated in 1×9.6 cm$^2$ gelatin-coated well in SG medium for 6 additional hours to remove any remaining contaminating somatic testis cells. After this final selection step on gelatin-coated plates, the cells were harvested as described above and plated into 1, 9.6 cm$^2$ well of MEFs and then maintained and propagated in SG Medium on MEFs as previously reported.

In addition to the specific steps described above, details for all cell culture conditions and materials and methods employed for deriving spermatogonial lines from Fischer F344 NHsd rats were performed as previously reported for deriving spermatogonial lines from strains of Sprague Dawley rats. See Wu, Z. et al., *Biol. Reprod.*, published on Mar. 18, 2009, as DOI:10.1095/biolreprod.108.072645.

Example 4

Restoring Fertility to Rats Deficient in the DAZ-Like (DAZL) Gene

The inventors discovered that, following cryopreservation, long-term cultures of proliferating spermatogonia could be used to restore fertility to rats with a severe form of azoospermia caused by reduced expression of the germ cell specific RNA binding-protein, DAZL. Additionally, the inventors determined that donor sperm stem cells effectively restore fertility to DAZL-deficient rats. Accordingly, this example illustrates transplantation of spermatogonia to restore fertility in sterile rats.

Animal Care and Use

Protocols for the use of rats in this study were approved by the Institutional Animal Care and Use Committee (IACUC) at UT-Southwestern Medical Center in Dallas. Rats used for this study were housed in individually ventilated, Lab Products 2100 cages in a dedicated room with atmosphere controls set to 72° F., 45-50% humidity during a 12 hour light/dark cycle (i.e. Light cycle=6:00 am-6:00 pm, Central Standard Time adjusted for daylight savings time). Rats were fed Harlan Teklad Irradiated 7912, LM-485 Mouse/Rat Diet, 5% fat Diet and a continuous supply of reverse osmosis water.

Rat Spermatogonial Lines

Seminiferous tubules were isolated from testes of 23-24 day old homozygous SD-Tg(ROSA-EGFP)2-4Reh Sprague Dawley rats. Rats of the SD-Tg(ROSA-EGFP)2-4Reh line were produced by pronuclear injection, and exhibit germ cell-specific expression of enhanced green fluorescent protein (EGFP) throughout male and female gametogenesis, and are referred to as GCS-EGFP rats. For deriving each spermatogonial line, seminiferous tubules were isolated from an individual rat and then enzymatically and mechanically dissociated into a cellular suspension to generate a testis cell culture. The testis cell culture was then used to isolate enriched populations of laminin-binding germ cells, which are highly enriched in spermatogonial stem cells. The laminin-binding fraction of germ cells was then used to derive proliferating cultures of spermatogonia [i.e. rat spermatogonial lines RSGL-GCS9 and RSGL-GCS10] in Spermatogonial Culture Medium (SG Medium). Passage 11, RSGL-GCS9 was thawed after 396 days of cryo-storage at –196° C. in SG Medium containing 10% DMSO (i.e. Spermatogonial Freezing Medium), and then sub-cultured in fresh SG Medium, for use in experiments between passage 13-17.

Germ Cell Transplantation and Colonization

The DAZL-deficient rat line was produced on a Sprague Dawley background and expresses a small hairpin RNA (shRNA) transgene designed to stimulate degradation of transcripts encoding DAZL. Rats in the DAZL-deficient transgenic line are male-sterile due to a defect in spermatogenesis; however, female rats from the same line remained fully fertile. To prepare recipients for transplantation of spermatogonia, heterozygous DAZL-deficient male rats or their wild-type litter mates were injected (i.p.) with 12 mg/kg busulfan (4 mg/ml in 50% DMSO) at 12 days of age. Busulfan is an alkylating agent cytotoxic to spermatogonia used to increase the effectiveness of spermatogonial transplantations, and clinically to combat cancer in humans. At 24 days of age (i.e., 12 days after busulfan treatment) donor tgGCS-EGFP rat spermatogonia harvested from culture at either passage 13 (culture day 158) or passage 17 (culture day 204) were loaded into injection needles fashioned from 100 µl glass capillary tubes at concentrations ranging from 2×10$^3$ to 1.5×10$^5$ EGFP$^+$ cells/50 µl culture media containing 0.04% trypan blue. The entire 50 µl volume was then transferred into the seminiferous tubules of anesthetized rats by retrograde injection through the rete of their right testes. The number of EGFP$^+$ colonies formed/testis were scored using an Olympus IX70 fluorescence microscope (Olympus, Inc) to visualize donor cell transgene expression in the seminiferous tubules at 30 days following transplantation. Images of recipient testis were taken with a Nikon SMZ1500 fluorescence stereomicroscope.

Morphometric Analysis of Rat Spermatogenic Cells/Histological Analysis of Rat Testes Spermatogenesis was evaluated in hematoxylin and eosin (H&E) stained, 3 µm thick histological sections prepared from testes of wild-type and DAZL-deficient littermates at 4 months of age, and from DAZL-deficient recipients at 212 days post-transplantation with spermatogonia (i.e. ~8 months of age). Prior to sectioning, the right testis of each animal was isolated, incubated overnight at 22-24° C. in Bouin's fixative, washed thoroughly in 70% ethanol and then embedded in paraffin. The average numbers of Sertoli cells, gonocytes, type-A spermatogonia (Type-A), intermediate to type-B spermatogonia (Type-B), pre-leptotene spermatocytes (PL), leptotene to early pachytene spermatocytes (L-EP), mid-pachytene to diplotene spermatocytes (MP-D), round spermatids (RS) and elongating spermatids (ES) were scored/tubular cross section. Sections were prepared from triplicate animals for each genotype. Numbers of cells per tubular cross-section were counted for each of the above categories by morphometric analysis using the Simple PCI software (Simple-PCI, Inc.) in line with an AX70 light microscope (Olympus, Inc). Cells in cross sections of each rat were counted in microscopic fields of 15,400 µm² (140 µm×110 µm) from at least 30 tubules/rat, n=3 rats/strain. Average counts for each cell type were normalized per 1000 Sertoli cells from triplicate rats of each group. Spermatogenic cell types in wild-type rats were classified based on their morphologies in the H&E-stained sections and localization to specific stages of a seminiferous epithelial cycle. The spermatogenic stage of each tubule used to count spermatogonia and Sertoli cells was verified in parallel cross-sections (3 µm) stained by the periodic acid-Schiff method in order to visualize steps of rat spermiogenesis. In DAZL-deficient rats, spermatogonia were classified as either undifferentiated (Unclip or differentiated (Dif) based on their patterns of H&E staining in comparison to wild-type rats. This was due to the inability to clearly identify distinct spermatogenic stages in the DAZL-deficient rats.

Histological Analysis of Spermatogonial Types

In wild-type rats, the numbers of undifferentiated and differentiating spermatogonia per tubular cross section were first scored at stages VIII, XI, XIII, XIV, II and V of spermatogenesis to avoid scoring differentiating spermatogonia in M-phase. Undifferentiated spermatogonia were clearly distinguished from differentiating types during each stage due to their relative lack of nuclear staining. As bright field images, undifferentiated spermatogonia were lightly stained throughout the cytoplasm and nucleus, and appeared "pinkish" compared to differentiating types of spermatogonia. Between stages V and VII, nucleoli $A_{a1}$ spermatogonia became more prominent as they differentiated into type A1 spermatogonia. In contrast, types A1 to B spermatogonia showed increasingly darker staining in distinct regions of their chromatin as they differentiated. Types A1 and A2 spermatogonia often showed "spots" of darkly stained chromatin situated randomly in the nucleus, which sharply contrasted from lighter staining chromatin throughout the rest of the nucleus. Nuclei of types A1 and A2 spermatogonia were clearly distinct from nuclei of undifferentiated spermatogonia. Types A3 to B spermatogonia also showed dark patterns of chromatin staining with increasing peri-nuclear localization of the most intensely stained regions.

Fluorometric Analysis of EGFP in Rat Testes

Seminiferous tubules of recipient animals were dissected from the testes of 24 day old rats and then homogenized in 1.5 ml of ice-cold lysis buffer [50 mM HEPES pH 8.0, 150 mM NaCl, 1 mM EDTA, 10% glycerol, 1% TritonX-100, 10 µg/ml aprotinin, 10 µg/ml leupeptin and 1 protease inhibitor tablet/12.5 ml] for 30 seconds using a PTA-7 probe on setting 5 of a PT10-35 polytron (Kinematica). The homogenates were incubated on ice for 15-20 min and then centrifuged at 3000×g for 10 min at 4° C. in a GPR table-top centrifuge (Beckman, Inc.). The supernatant solutions were centrifuged at 15,800×g for 10 min at 4° C. in a micro-centrifuge (Model 5042, Eppendorf, Inc.), and the resultant supernatant fractions were then stored at −80° C. Frozen supernatant solutions were thawed on ice and then further clarified by centrifugation at 230,000×g, $r_{av}$ (tla-100.3 rotor, TL1000 ultracentrifuge, Beckman, Inc.) for 30 min at 4° C. Standards and supernatant solutions from the final centrifugation step were diluted into assay buffer [100 mM sodium bicarbonate, pH 9.6] and then analyzed for fluorescent intensity using a FL600 fluorescence micro-titer plate reader (BioTek, Inc.) equipped with filter wheel sets for maximal excitation at 485 nm and maximal emission at 516 nm. Affinity purified recombinant EGFP with a carboxyl-terminal histidine tag (rEGFP-His) was used as a standard for determining equivalents of EGFP in lysates prepared from testes of recipient animals. The rEGFP-His was produced by transient expression from the vector pcDNA6.0-EGFP-V5-His-B following transfection (Fugene 6 transfection reagent, Roche, Inc.) into COS-7 cells as previously described.

Genotyping Progeny from Recipient Rats

Transgenic rat progeny from crosses between wild-type recipients and wild-type females were genotyped by PCR analysis of genomic DNA using primers specific to the EGFP transgene, and the LTR region of the lentiviral transgene used to produce the DAZL-deficient rat line; primers to GAPDH were used to amplify loading controls. Transgene copy number in F2 progeny from hemizygous crosses between F1 progeny of recipients and wildtype females was determined by qtPCR using primers to EGFP and the 18S ribosomal subunit. Genotyping results were verified by Southern blot hybridization assays of genomic DNA digested with Xmn1 and Xba1 using a probe specific for the EGFP transgenes, and for olfactory marker protein as a loading control. The EGFP probe was isolated as a Nhe1/EcoR1 fragment from pLE-GFP-C1 (Clonetech, Inc.). The OMP probe was isolated as a BamH1 fragment from pTOPO-XL:OMP corresponding to base pairs 14268243-14269267 of NW_047561; GI:34857865; RGSC v3.4. EGFP PCR primers: 5'-GTCTCGTGACCCTGACCTACGG-3' and 5'-ATGC-CCTTCAGCTCGATGCGG-3; Rat GAPDH PCR primers: 5'-ATGATTCTACCCACGGCAAG-3' and 5'-GCTAAG-CAGTTGGTGGTGCA-3'; Lentiviral transgene PCR primers to LTR region: 5'-AACAGGGACTTGAAAGCG-3' and 5'-ATACTGACGCTCTCGCACCC-3'. Genotyping results were also confirmed in representative progeny by direct visualization of EGFP transgene expression in testes and ovaries using a Nikon SMZ1500 fluorescence stereomicroscope.

Inventors morphologically determined that DAZL-deficient rats revealed normal numbers of spermatogonia, but reduced numbers of spermatocytes and round spermatids in their seminiferous tubules, culminating in a severe failure to produce elongating spermatids. Although DAZL-deficient rats fail to produce elongated spermatids, they appear to express an intact spermatogonial stem cell compartment, as evidenced by both undifferentiated and differentiating populations of spermatogonia within seminiferous tubules of adult animals. The presence of a functional spermatogonial stem cell compartment was verified by in vivo spermatogenesis colony forming assays in which genetically tagged donor spermatogonia were thawed from cryo-storage, propagated over multiple passages in culture, and then transplanted into seminiferous tubules of busulfan-treated, DAZL-deficient rat testes.

Donor spermatogonial lines were derived from testes of individual Germ Cell Specific (GCS)-EGFP transgenic rats, which robustly expressed EGFP as a vital marker specifically during all known steps of gametogenesis. The DAZL-deficient recipient rat line also expresses EGFP from its transgene, but at relatively low levels. By comparison, EGFP is 20-fold more abundant in testes of GCS-EGFP rats than in DAZL-deficient rats (FIG. 1A). Thus, development of donor spermatogonia from GCS-EGFP rats was clearly detected following transplantation into DAZL-deficient rat testes, which they colonized 3-fold more efficiently than wildtype recipient testes (FIG. 1B).

Figure 2:
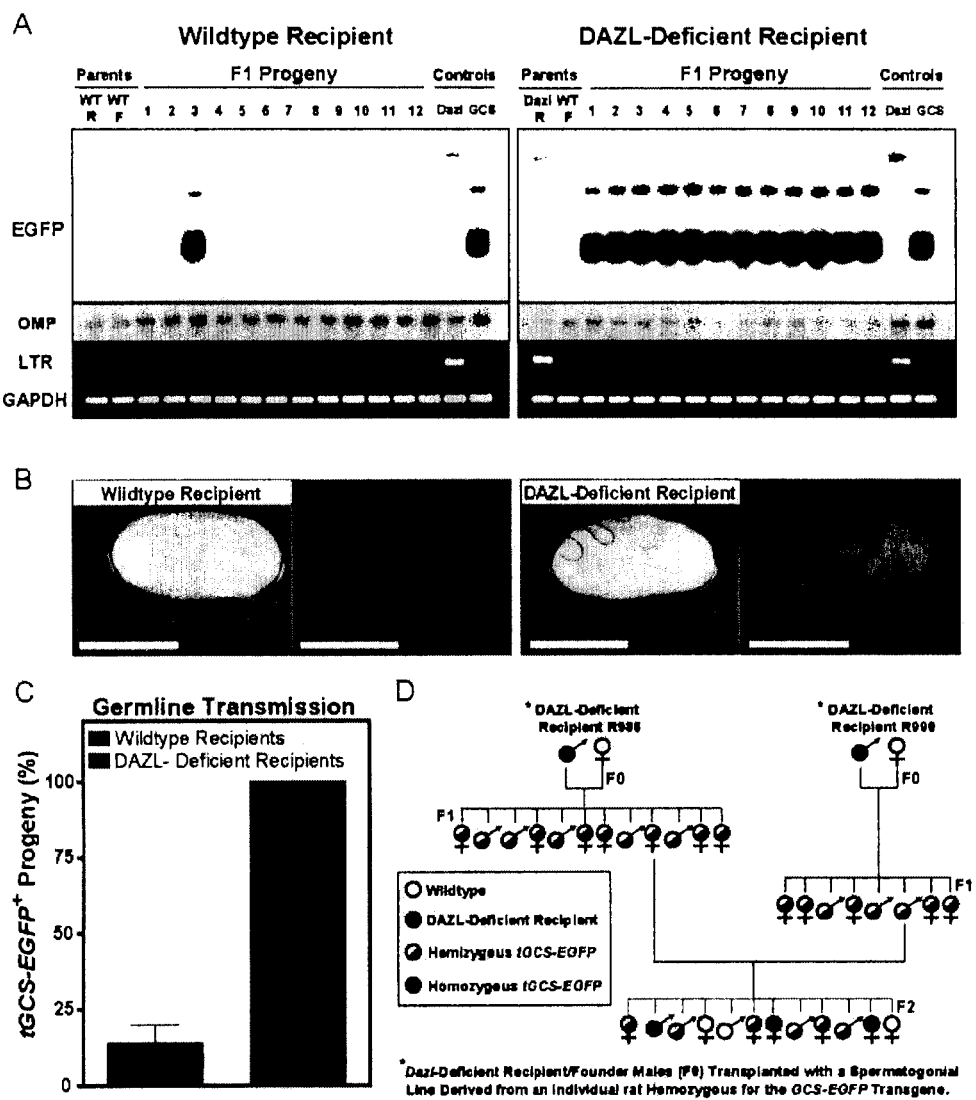
FIG. 2. Maximal Germline Transmission from DAZL-Deficient Rats. (A) Southern blot analysis of progeny from Wildtype (WT) and DAZL-Deficient (Dazl) recipient rats with right testes transplanted with 50,000 GCS-EGFP spermatogonia at passage 13 (i.e., 158 days in culture); the left testis of each animal was not transplanted. At 75 days post-transplantation recipients (R) were paired with WT females (F) and allowed to produce pups by natural breeding (See R942-R949 in Table 1). Shown are blots from representative litters probed for EGFP to distinguish progeny produced by donor cells from their recipient-fathers and wildtype mothers. OMP=loading control probe for genomic DNA on blots. Genomic DNA samples used for Controls on each blot were from untreated GCS-EGFP and DAZL-Deficient transgenic rats. LTR=PCR primers specific for detecting the lentiviral transgene used to make DAZL-deficient rats. GAPDH=PCR primers for genomic DNA loading control. (B) Bright field and green fluorescence images of testes from Wildtype (Left) and DAZL-deficient (Right) recipient rats at 212 days post-transplantation. Scale bar=1 cm. (C) Graph of germline transmission rates by natural breeding for the donor GCS-EGFP transgene from Wildtype and DAZL-deficient recipient rats that had their right testis transplanted with 50,000 GCS-EGFP spermatogonia at passage 13; the left testis of each animal was not transplanted. DAZL-deficient recipients transmitted the GCS-EGFP transgene to 100%+/−0% of progeny (+/−SEM, n=3 recipients; 9 litters), with 73 of 73 total F1 pups born from donor cells. Wildtype recipient littermates transmitted the GCS-EGFP transgene to 14%+/−5.9% of progeny (+/−SEM, n=3 recipients; 9 litters), with 16 of 116 total F1 pups born from donor cells. (D) Genealogy tree showing stable transmission of donor cell haplotypes from DAZL-Deficient recipient/founders (F0) R989 and R990 to F1 and F2 progeny. Recipients were each transplanted with 150,000 rat spermatogonia/testis from line RSGL-GCS9 at passage 17 (See R988-R990 in Table 1). Spermatogonial line RSGL-GCS9 was derived from a rat homozygous for the GCS-EGFP transgene. Thus, F1 progeny represent half-siblings; some of which were crossed to re-derive transgenic F2 progeny homozygous for the tgGCS-EGFP allele.
Figure 3:
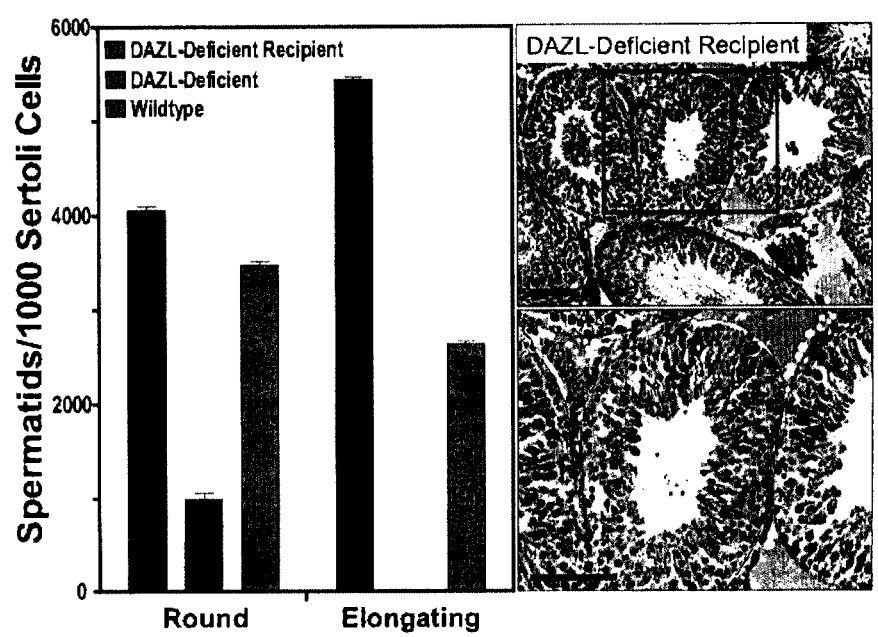
FIG. 3. Long-Term Spermatogenesis Colonizing Potential of Donor Spermatogonia (Left) Graph showing relative numbers of Round and Elongating Spermatids in seminiferous tubules of non-transplanted, non-busulfan-treated, Wildtype and DAZL-deficient rat lines at 4 months of age (see FIG. 1a), in comparison to Spermatid numbers in busulfan-treated, DAZL-deficient recipient rats at 212 days (i.e. ~8 months of age) after being transplanted with rat spermatogonial line, RSGL-GCS9, at passage 13 (i.e. culture day 158). Cell counts were normalized/1000 Sertoli cells. +/−SEM, n=3 rats/group. (Right) Images of histological sections of seminiferous tubules from the DAZL-deficient recipient rats described in the "Left" panel after being transplanted with spermatogonia from RSGL-GCS9. Bottom Right shows a higher magnification image within the boxed region of the Top Right panel. Scale bars=100 μm.

The transplanted spermatogonial stem cells effectively developed into functional spermatozoa, which due to the absence of sperm competition, transmitted the donor cell haplotype to progeny >7-fold more efficiently from DAZL-deficient recipients than from wildtype litter mates (FIG. 2A-C; Table 1). In each DAZL-deficient recipient, spermatogenesis was regenerated from the spermatogonial lines that had proliferated in culture (>2 million-fold expansion in cell number) for 5-7 months, yielding 100% germline transmission of the donor haplotype to F1 progeny by natural mating (FIG. 3A-C; Table 1). The GCS-EGFP transgene was further transmitted at Mendelian ratios from F1 to F2 progeny (26% wildtype, 48% heterozygous, 26% homozygous; 81 total pups; n=6 litters) (FIG. 2D). No evidence of tumor formation was observed in any of the recipients or progeny. The regenerative effects of the spermatogonial lines on fertility were also apparent upon histological examination of testes from DAZL-deficient recipients at 212 days following transplantation; 57±6.1% (±SE, n=3) of their seminiferous tubules contained colonies of spermatogenesis that developed to the elongating spermatid stage (FIG. 3). This represented a >2000-fold increase in the relative number of elongating spermatids scored/number of Sertoli cells in transplanted versus non-transplanted DAZL-deficient rat testes (FIG. 3).

This is believed the first use of a biochemically tagged, donor spermatogonial line to restore fertility in azoopermic (DAZL-deficient) transgenic rats. Thus, fertility was safely restored to all recipients transplanted with spermatogonial lines after long-term proliferation in a recently formulated spermatogonial culture medium as described in Example 2 above. Surprisingly, as few as 50,000 donor spermatogonia transplanted into only a single testis/recipient are able to effectively restore fertility to azoospermic rats with 100% progeny being derived from the cultured cells after thawing from cryopreservation. The donor spermatogonial lines were able to colonize seminiferous tubules of DAZL-deficient recipients 3-fold more effectively than tubules of wildtype litter mates, and transmission of the donor cell haplotype by natural mating was 7-fold greater from DAZL-deficient recipients. This difference in transmission rate by donor versus endogenous germlines for each recipient model was associated with two apparent factors: 1) greater colonization efficiencies by donor spermatogonia in DAZL-deficient rat testes, and 2) the relative lack of sperm competition produced by DAZ-deficient rats.

Example 5

Library of Spermatogonial Stem Cells Created by Transposon Mediated Gene Knockout/in Mutants/Clonal Expansion and Selection of Single Clone Inventors successfully applied spermatogonial stem cells to establish transposon mutagenesis in the rat by taking advantage of the highly efficient genomic insertion of a transposon (for example Sleeping Beauty) equipped with a gene trap cassette. Inventors carried out a small-scale pilot screen that allowed the isolation of >150 gene trap insertions after appropriate selection of clonally enriched spermatogonia in vitro. Transposon insertions were mapped into genes, some of which are implicated in blood pressure, renal function, cholesterol metabolism and other biological processes relevant to human health. Selected spermatogonial stem cell lines were transplanted into the testes of recipient rats to allow spermatogenesis resulting in genetically modified spermatozoa in vivo. Recipient males were paired with wild-type females for transmission of genetically modified spermatogonial genomes directly to rat progeny by natural mating. Thus, by merging the cellular biology of spermatogonia with state-of-the-art transposon technology, inventors have generated an experimental pipeline for creating knockout rats using clonally expanded cultures of germline stem cells.

In order to transmit stem cell genomes through the rat germline, spermatogonial lines containing gene trap Sleeping Beauty insertions were selected in culture and transplanted to repopulate testes of sterilized, recipient rats. Testes of DAZL-deficient and wild-type recipient rats were transplanted with mixed populations of G418-resistant spermatogonial lines selected as a library estimated to contain ~200,000 individual clonal lines with trapped genes (i.e., gene trapping frequency=0.4% transfected cells×15-20% transfection efficiency×3×10$^6$ cells/transfection). Rat progeny from these crosses were genotyped using PCR primer sets designed to specifically detect the β-geo cassette within stably integrated Sleeping Beauty, and the GCS-EGFP rat transgene cassette as an inheritable marker for the donor spermatogonial line. No donor-derived pups were detected in litters born from the wild-type female and recipient pair (0/56 pups born; n=6 litters) using the G418-selected spermatogonia. However, litters born from a wild-type female and DAZL-deficient recipient pair yielded 100% germline transmission of the GCS-EGFP+ donor cell haplotype (113/113 pups born; n=16 litters), wherein the β-geo, Sleeping Beauty marker was transmitted to 72% of total F1 progeny, averaging 69.2±29.7% GCS-EGFP+/β-geo+ pups/litter (mean±SD; 82/113 pups total born; n=16 litters). Thus, the inventors have shown that cultures of spermatogonial stem cells can be genetically modified with Sleeping Beauty transposons in culture, clonally enriched for gene-trap mutations by selection in G418-containing medium, and then used to produce mutant rats by natural breeding. In each rat line, the defined Sleeping Beauty genomic mutation accurately predicted disruption of gene expression at the transcript and protein levels.

Plasmids and HeLa Cell Transfections

To generate the gene trap transposon vector, a 4.3-kb SAβ-geopA cassette consisting of a splice acceptor (SA—intron/exon2 boundary of adenovirus), lacZ-neomycin phosphotransferase fusion (β-geo) and polyadenylation signal from bovine growth hormone gene was cut out of the pSAβ-geo vector with XhoI. The ends were blunted with Klenow polymerase and ligated to SpeI linkers (NEB), after which the SAβ-geopA cassette was cloned into a Sleeping Beauty vector in which the left inverted repeat of the element had been doubled HeLa cells were seeded at a density of ~3×10$^5$ cells per well on 6-well plates 24 hrs prior to transfection. Plasmids containing transposon and transposase were transfected in ratios 1:1, 10:10, 1:10 and 10:1 (1=50 ng, 10=500 ng). Reactions were filled up to a total of 1 µg with FV4a (CAT) plasmid. In the negative control, the transposase containing plasmid was replaced with the same amount of a Caggs-CRE plasmid. Transfection reagent used was JetPEI™-RGD (2 µl JetPEI™-RGD+98 µl 150 mM NaCl mix added to 100 µl plasmid/150 mM NaCl mix per each sample). 48 hrs after the transfection cells were trypsinized and ⅕ (200 µl of 1 ml suspension) of the cells from each transfected well were re-plated to 10 cm plates and put on G418 selection (0.6 mg/ml). X-gal staining was done using a modified protocol of Sanes et al. (1986). Briefly, cells were washed with PBS, fixed 5 min at RT in 2% formaldehyde plus 0.2% glutaraldehyde in PBS and then rinsed with PBS and overlaid with the histochemical reaction mixture containing 1 mg/ml X-Gal, 5 mM potassium ferricyanide, 5 mM potassium ferrocyanide, 2 mM MgCl$_2$, 0.75 mM HCl and 0.1% Tween-20 in PBS and incubated in 37° C. for 24 hrs.

PCRs

Splinkerette PCR was completed using a Csp6I restriction digest of the genomic DNA, and LacZ-specific primer pUC3 5'-cga tta agt tgg gta acg cca ggg-3' and transposon inverted repeat-specific primer T-BalRev 5'-ctt gtc atg aat tgt gat aca gtg aat tat aag tg-3' in addition to the linker-specific primers. For reverse transcription PCR (RT-PCR), 5 µg DNAseI-treated RNA was reverse-transcribed using the LacZ-specific primer 5'-ttc tgc ttc atc agc agg ata tcc-3' and SuperScriptIII (Invitrogen). The single-stranded DNA was PCR-amplified by LacZ-specific primer LacZ2 5'-acc acg ctc atc gat aat ttc acc-3' and gene-specific primer Tbc1d1-P1 5'-atc act tgt gag cac gca ggg aat a-3', and further amplified with nested primers ZRT 5'-gat tga ccg taa tgg gat agg-3' and Tbc1d1-P2 5'-aag gga agg gag ggc atc tag tcc t-3. PCR products were cloned into pGEM-T (Promega) and sequenced. Real-time PCR was used for measuring relative transcript abundance of trapped genes expressed in rat tissues. Total RNA was extracted from brain and skeletal muscle using the Trizol reagent (Ambion). The extracted RNA was quantified using the Pico-Green assay (Invitrogen). cDNA was synthesized by priming 100 ng total RNA from each tissue using random primers as previously described. Relative levels of HIP2 and TBC1D1 transcripts in tissues of each rat were then measured by qtPCR using SYBR green dye as described. PCR primer sets were designed to specifically amplify HIP2 flanked boundaries of intron 1, 2, 4, 5. PCR primer sets were designed to specifically amplify TBC1D1 flanked boundaries of intron 1, 2, 3, and 4.

Rat Spermatogonial Stem Cell Lines

Rat spermatogonial lines, RSGL-GCS3 and RSGL-GCS9, was derived using highly pure populations of undifferentiated spermatogonia isolated from the germ cell specific-EGFP (GCS-EGFP) transgenic line of Sprague Dawley rats. The GCS-EGFP rat line expresses EGFP specifically during all stages of gametogenesis. Undifferentiated spermatogonia used to derive RSGL-GCS3 and RSGL-GCS9 were isolated from rat seminiferous tubules based on the principle that testicular somatic cells bind tightly to plastic and collagen matrices when cultured in serum-containing medium, whereas spermatogonia and spermatocytes do not bind to plastic or collagen when cultured in serum-containing medium. The isolated spermatogonia provide a highly potent and effective source of stem cells that have been used to initiate in vitro and in vivo culture studies on spermatogenesis. RSGL-GCS3 was originally derived, sub-cultured and maintained on feeder layers of irradiated, DR4 mouse embryonic fibroblasts (MEFs) in Shinohara's Medium minus serum and vitamin-A, until frozen in cryo-storage. Upon thawing for the current study, RSGL-GCS3 was propagated on DR4 MEFs using Spermatogonial Culture Medium (SG Medium). RSGL-GCS9 was originally derived, sub-cultured and maintained on feeder layers of irradiated, DR4 MEFs at $4.5 \times 10^4$ cells/cm$^2$ in SG Medium until frozen in cryo-storage, prior to thawing for production of mutant rats in the current study, as described below.

Transfection of Rat Spermatogonial Lines with Sleeping Beauty Constructs and Selection of Gene Trap Insertions Spermatogonial line RSGL-GCS3, was thawed after cryo-storage at passage 8 in a spermatogonial freezing medium (SG Freezing Medium) and then expanded to passage 10 in fresh SG Medium before harvesting for Nucleofection with Sleeping Beauty Plasmids. Spermatogonial line RSGL-GCS9 was thawed after cryo-storage at passage 9 in SG Freezing Medium and then expanded to passage 11 in fresh SG Medium before harvesting for Nucleofection with Sleeping Beauty Plasmids. The harvested spermatogonia were transfected with DNA test constructs using 10 µg total DNA in a suspension of $3 \times 10^6$ spermatogonia/100 µl Nucleofection Solution L (Amaxa, Inc.) using settings A020 on the Nucleofector (Amaxa, Inc.). For genetic modification of the rat spermatogonial lines with a hyperactive Sleeping Beauty transposon/transposase system, a ~1:30 ratio of the transposase to transposon plasmids was used for these transfections (i.e., 0.33 µg transposase:9.67 µg transposon/100 µl Nucleofection Solution L).

Following transfection, the spermatogonia were plated directly into SG Medium at an equivalent of ~$2.5 \times 10^5$ nucleofected cells/9.5 cm$^2$ onto freshly prepared irradiated MEFs. On day 7 following nucleofection, cultures were maintained in SG medium containing 75 µg/ml G418 (Invitrogen, Inc.) for an additional 10 days to select for cells that contained gene trap insertions. Cultures were fed fresh SG medium with G418 every two days. After this selection period, cultures were maintained in SG-medium without G418. Following nucleofection, fresh MEFs ($2 \times 10^4$/cm$^2$) were added into ongoing cultures of spermatogonial colonies every 10-12 days prior to passaging. At 35-45 days following nucleofection, individual colonies were picked from cultures using a p200 Eppendorf tip and then the colonies were transferred into wells of a 96-well plate for Monoclonal expansion of the germlines. In parallel, all of the colonies from the second six well plate from the same transfection were harvested and pooled together for Polyclonal expansion of rat germlines for an additional 35 days following selection in G418 to sufficient numbers for both their cryopreservation (Duplicate vials at $2 \times 10^6$ cells/line) in liquid nitrogen, and for their transplantation into recipient rat testes ($1.5-3 \times 10^5$ cells/rat), as described below.

Spermatogonial Transplantation

The DAZL-deficient rat line was produced on a Sprague Dawley background and expresses a small hairpin RNA (shRNA) transgene designed to stimulate degradation of transcripts encoding DAZL. Rats in the DAZL-deficient transgenic line are male-sterile due to a defect in spermatogenesis; however, female rats from the same line remained fully fertile. To prepare recipients for transplantation of spermatogonia, heterozygous DAZL-deficient male rats or their wildtype litter mates were injected (i.p.) with 12 mg/kg busulfan using our established protocol. At 12 days post-busulfan treatment of the recipients, the G418-resistant donor spermatogonia were harvested from culture and loaded into injection needles at concentrations ranging at $3-6 \times 10^5$ spermatogonia/50 µl culture media containing 0.04% trypan blue (Sigma). The entire 50 µl volume was then transferred into the seminiferous tubules of anesthetized rats by retrograde injection through the rete of their right and left testis. Rats used for this study were housed in individually ventilated, Lab Products 2100 cages in a dedicated room with atmosphere controls set to 72° F., 45-50% humidity during a 12 hour light/dark cycle. Rats were fed Harlan Teklad Irradiated 7912, LM-485 Mouse/Rat Diet, 5% fat Diet and a continuous supply of reverse osmosis water. Protocols for the use of rats in this study were approved by the Institutional Animal Care and Use Committee (IACUC) at UT-Southwestern Medical Center in Dallas, as certified by the Association for Assessment and Accreditation of Laboratory Animal Care International (AALAC).

Genotyping Mutant Rat Progeny from Transplanted Recipient Rats

Genotyping primers were specific to the beta-Geo and EGFP transgenes, and the LTR region of the lentiviral transgene used to produce the DAZL-deficient rat line; primers to GAPDH were used to amplify loading controls. Genotyping results were verified by Southern blot hybridization assays of genomic DNA digested with XmnI and XbaI using a probe specific for the EGFP transgenes, and for olfactory marker protein (OMP) as a loading control, and the LacZ portion of the Beta-Geo insert in the Sleeping Beauty transposon construct. The EGFP probe was isolated as a NheI/EcoRI fragment from pLEGFP-C1 (Clonetech, Inc.). The OMP probe was isolated as a BamHI fragment from pTOPO-XL:OMP corresponding to base pairs 14268243-14269267 of NW_047561; GI:34857865; RGSC v3.4.

Western Blotting

Proteins were extracted from dissected testes and then homogenized in 1.5 ml of ice-cold lysis buffer (50 mM HEPES, pH 8.0, 150 mM NaCl, 1 mM EDTA, 10% glycerol, 1% Triton X-100, 10 µg/ml aprotinin, 10 µg/ml leupeptin and 1 protease inhibitor tablet/12.5 ml) for 30 s using a PTA-7 probe on setting 5 of a PT10-35 polytron (Kinematica). The homogenates were incubated on ice for 15-20 min and then centrifuged at 3000×g for 10 min at 4° C. in a GPR tabletop centrifuge (Beckman, Inc.). The supernatant solutions were centrifuged at 15,800×g for 10 mM at 4° C. in a microcentrifuge (Model#5042, Eppendorf, Inc.), and the resultant supernatant fractions were then stored at −80° C. Frozen supernatant solutions were thawed on ice and then further clarified by centrifugation at 230,000×g, rav (tla-100.3 rotor, TL1000 ultracentrifuge, Beckman, Inc.) for 30 min at 4° C. Protein (100 µg per pooled sample per lane) was separated on SDS gels (10-20% acrylamide gradient, Invitrogen, Inc.) and transferred to nitrocellulose membranes. Nonspecific, proteinbinding sites were blocked by incubating membranes overnight at 4° C. in blocking buffer: TBST (Tris-buffered saline with Tween-20: 10 mM Tris-HCl, pH 7.5, 150 mM NaCl, 0.1% Tween-20) containing 5% nonfat dry milk. Membranes were washed three times in TBST and incubated for 1 h at 22-24° C. with diluted primary antibody (1/1000 HIP2; 1/300 TBC1D1) in blocking buffer. Membranes were washed three times in TBST (0.3% Tween-20) and incubated 45 min, 22-24° C. with peroxidase-conjugated, anti-mouse IgG diluted 1:50,000 in blocking buffer. Membranes were washed three times in TBST and protein bands detected using the enhanced chemiluminescence detection method (ECL, Amersham, Inc.).

In summary, the invention is technically less difficult, less expensive, and less time-consuming to implement than conventional technologies in this field. The invention also guarantees maximal levels of germline transmission of mutated genes to rat progeny, by either natural mating or assisted reproduction.

TABLE 1

Progeny from Wildtype and DAZL-Deficient Recipient Rats Transplanted with GCS-EGFP Rat Spermatogonia

| Recipient | Recipient Background | Passage Number | Days to Analysis | Gram wt per R, L testis | Cells per R, L testis | Days to first litter | Number Litters | Average Litter Size | Total Pups Born | Pups Born from Transplanted Stem Cells (%)* |
|---|---|---|---|---|---|---|---|---|---|---|
| R946 | Wildtype | p13 | 212 | 0.569, 0.341 | 50,000:0 | 127 | 3 | 11.3 | 34 | 3 (8.8) |
| R948 | Wildtype | p13 | 212 | 0.735, 0.278 | 50,000:0 | 131 | 3 | 10 | 30 | 11 (36.7) |
| R949 | Wildtype | p13 | 212 | 1.054, 0.201 | 50,000:0 | 113 | 3 | 17.3 | 52 | 2 (3.8) |
| Average | | p13 | 212 | 0.786, 0.273 | 50,000:0 | 123.7 | 3 | 12.9 | 38.7 | 4.3 (16.4) |
| R942 | DAZL-Def | p13 | 212 | 0.572, 0.286 | 50,000:0 | 154 | 3 | 8.7 | 26 | 26 (100) |
| R943 | DAZL-Def | p13 | 212 | 0.651, 0.377 | 50,000:0 | 141 | 3 | 7.7 | 23 | 23 (100) |
| R944 | DAZL-Def | p13 | 212 | 0.511, 0.326 | 50,000:0 | 156 | 3 | 8 | 24 | 24 (100) |
| Average | | p13 | 212 | 0.578, 0.330 | 50,000:0 | 150 | 3 | 8.1 | 24.3 | 24.3 (100) |
| R988 | DAZL-Def | p17 | 236 | 0.523, 0.578 | 150,000:150,000 | 122 | 3 | 12.7 | 38 | 38 (100) |
| R989 | DAZL-Def | p17 | 236 | 0.489, 0.439 | 150,000:150,000 | 128 | 3 | 9.3 | 28 | 28 (100) |
| R990 | DAZL-Def | p17 | 236 | 0.487, 0.371 | 150,000:150,000 | 136 | 3 | 5.3 | 16 | 16 (100) |
| Average | | p17 | 236 | 0.499, 0.427 | 150,000:150,000 | 128.6 | 3 | 9.1 | 27.3 | 27.3 (100) |

Wildtype or DAZL-deficient (DAZL-def) recipient rats were transplanted with either 0.5 or 1.5 × 10$^5$ EGFP$^+$ cells/testis from rat spermatogonial line GCS9 at 12 days after busulfan treatment (i.e. 12 mg/kg i.p.) on postnatal day 24. At ~75 days post-transplantation recipients were paired with 75-80 day old wildtype female rats. Spermatogonia line GCS9 was harvested from passages number 13 and 17, which corresponded to 158 and 204 days in culture, respectively, prior to their transplantation.
Recipients R942-R949 were littermates born from a hemizygous, transgenic DAZL-deficient female and a wildtype Sprague Dawley male. No progeny were born from breeder pairs of un-transplanted, busulfan-treated DAZL-deficient males and wild-type females (n = 3 breeder pairs). Breeder pairs of untreated, wild-type male litter mates of DAZL-deficient rats and wild-type female rats from Harlan, Inc. produced 15.5 ± 4.5 pups/litter (+/−SEM, n = 8 litters from 3 breeder pairs).
*Percent GCS-EGFP$^+$ F1 progeny.

TABLE 2

Components of Rat Spermatogonial Culture Media

| SA Medium* (concentration) | SR-LE-Medium** (concentration) | SG Medium** (concentration) | RSFM*** (concentration) | B27-Vitamin A Supplement **** |
|---|---|---|---|---|
| StemPro basic (1x) | StemPro basic (1x) | DMEM: HamsF12 (1x) | MEM α (1x) | d-Biotin |
| Anti-biotic/mycotic (1x) | Anti-biotic/mycotic (1x) | Anti-biotic/mycotic (1x) | Penicillin (50 units/ml) | BSA, fatty acid free Fraction V |
| L-glutamine (2 mM) | L-glutamine (2 mM) | L-glutamine (6 mM)† | Streptomycin (50 µg/ml) | Catalase |
| 2-mercaptoethanol (50 µM) | 2-mercaptoethanol (100 µM) | 2-mercaptoethanol (50 µM) | I-glutamine (2 mM) | L-Carnitine HCl |
| Glucose (6 mg/ml) | Glucose (6 mg/ml) | B27-vitamin A Supp. (1x) | 2-mercaptoethanol (100 µM) | Corticosterone |
| MEM vitamin (1x) | MEM vitamin (1x) | Rat GDNF (20 ng/ml) | Hepes (10 mM) | Ethanolamine HCl |
| NEAA (1x) | NEAA (1x) | Human bFGF (20 ng/ml) | palmitic acid (4.8 µM) | D-Galactose (Anhyd.) |
| Estradiol (30 ng/ml) | Estradiol (30 ng/ml) | | palmitoleic acid (0.42 µM) | Glutathione (Reduced) |
| Pyruvic Acid (30 µg/ml) | Pyruvic Acid (30 µg/ml) | | stearic acid (1.76 µM) | Insulin (Human, recombinant) |
| Lactic Acid (1 µl/ml) | Lactic Acid (1 µl/ml) | | oleic acid (2.0 µM) | Linoleic Acid |
| Ascoribic Acid (100 µM) | Ascoribic Acid (100 µM) | | linolenic acid (5.4 µM) | Linolenic Acid |
| B27-vitamin A Supp. (1x) | B27-vitamin A Supp. (1x) | | linoleic acid (0.85 µM) | Progesterone |
| Rat GDNF (10 ng/ml) | Rat GDNF (10 ng/ml) | | GFR α 1 (300 ng/ml) | Putrescine•2HCl |
| Human bFGF (10 ng/ml) | Human bFGF (10 ng/ml) | | Murine LIF (1000 units/ml) | Sodium Selenite (1000X) |
| StemPro Supplement (1x) | StemPro Supplement (1x) | | Rat GDNF (40 ng/ml) | Superoxide Dismutase |
| Mouse EGF (20 ng/ml) | | | Human bFGF (1 ng/ml) | T-3/Albumin Complex |

TABLE 2-continued

Components of Rat Spermatogonial Culture Media

| SA Medium* (concentration) | SR-LE-Medium** (concentration) | SG Medium** (concentration) | RSFM*** (concentration) | B27-Vitamin A Supplement **** |
|---|---|---|---|---|
| Murine LIF (1000 units/ml) | | | Insulin (25 μg/ml) | DL Alpha-Tocopherol |
| Insulin (25 μg/ml) | | | Apo-transferrin (100 μl/ml) | DL Alpha Tocopherol Acetate |
| Biotin (10 μg/ml) | | | Putrescine (120 μM) | Transferrin (Human, Iron-Poor) |
| Progesterone (60 ng/ml) | | | Na₂SeO₃ (60 nM) | |
| Apo-transferrin (100 μg/ml) | | | BSA (6 mg/ml) | |
| Putrescine (60 μM) | | | | |
| Na₂SeO₃ (30 nM) | | | | |
| BSA (5 mg/ml) | | | | |

TABLE 3

Vendor and Catalog numbers for SA and SG media components

| Component | Supplier, Catalog Number |
|---|---|
| 1. Base Media/Nutrient Supplements: | |
| StemPro34 SFM Base | Invitrogen, 10639-011 |
| 40x StemPro34 nutrient supplement | Invitrogen, 10639-011 |
| Dulbecco's Modified Eagle's Medium:HamsF12 nutrient mix (1:1)* | Sigma, D8437 |
| B-27 Supplement minus vitamin A* | Invitrogen, 12587-010 |
| 2. Added Small Molecule/Nutrient Components: | |
| d-(+) Glucose | Sigma, G7021 |
| L-glutamine* | Invitrogen, 25030-149 |
| 50x Antibiotic-Antimycotic* | Invitrogen, 15240-062 |
| 50x MEM Vitamins | Invitrogen, 11120-052 |
| 50x Non-essential Amino Acids | Invitrogen, 11140-050 |
| d-Biotin | Sigma, B4639 |
| Pyruvic Acid, Sodium Salt | Sigma, P4562 |
| dl-Lactic Acid (60% Solution) | Sigma, L7900 |
| Ascorbic Acid | Sigma, A4034 |
| Sodium Selenite | Sigma, S5261 |
| Putrescine | Sigma, P5780 |
| Progesterone | Sigma, P8783 |
| β-Estradiol 17-cypionate | Sigma, E8004 |
| 2-Mercaptoethanol* | Sigma, M3148 |
| 3. Added Polypeptide Components: | |
| Bovine Apo-transferrin | Sigma, T1428 |
| Bovine Serum Albumin | Calbiochem, 126609 |
| Bovine Insulin | Sigma, 11882 |
| ESGRO (mouse LIF) | Chemicon, ESG1107 |
| Recombinant mouse EGF | Sigma, E4127 |
| Recombinant human basic FGF* | Sigma, F0291 |
| Recombinant rat GDNF* | R&D Systems, 512-GF-050 |

What is claimed is:

1. A composition comprising an isolated rat spermatogonial stem cell and spermatogonial stem cells expanded therefrom and a culture medium, wherein the culture medium comprises: 1:1 ratio of Dulbecco's Modified Eagle Medium (DMEM) to Ham's F12 nutrient mixture, from about 10 ng/ml to about 30 ng/ml glial cell-derived neurotrophic factor (GDNF), from about 10 ng/ml to about 30 ng/ml Fibroblast Growth Factor-2 (FGF2), from about 50 to about 120 μM 2-mercaptoethanol, from about 3 mM to about 10 mM L-glutamine, and a 1× concentration of B27 minus vitamin A supplement solution.

2. The composition of claim 1, wherein the isolated stem cell is not DAZ-like (DAZL) deficient.

3. The composition of claim 1, wherein the isolated stem cell comprises SEQ ID NO:5 and SEQ ID NO:6.

4. The composition of claim 1, wherein the isolated stem cell is obtained from stem cells cultured from about 30 days to about 150.

5. The composition of claim 1, wherein the isolated rat spermatogonial stem cell is in culture between about 158 and about 204 days.

6. The composition of claim 1, wherein the isolated rat spermatogonial stem cell has a doubling time of between about 8 and about 9 days.

7. The composition of claim 1, wherein the isolated rat spermatogonial stem cell has a doubling time of no less than 8.4 days.

8. The composition of claim 1, wherein the isolated rat spermatogonial stem cell expands no less than about 20,000 times as compared to the number of cells seeded in culture.

9. The composition of claim 1, wherein the composition is frozen.

10. The composition of claim 1, wherein the isolated rat spermatogonial stem cell comprises one or more genetic mutations.

11. The composition of claim 10, wherein the isolated rat spermatogonial stem cell further comprises a nucleotide sequence flanking the one or more sites of the one or more genetic mutations comprising SEQ ID NO:5 and SEQ ID NO:6.

12. The composition of claim 1, wherein the isolated rat spermatogonial stem cell further comprises a nucleotide sequence encoding one or more heterologous amino acid sequences.

13. The composition of claim 12, wherein the one or more heterologous amino acid sequences is green florescent protein.

14. The composition of claim 1, wherein the isolated rat spermatogonial stem cell is resistant to G418.

15. The composition of claim 1, wherein the composition is free of somatic testis cells.

16. The composition of claim 1, wherein the composition further comprises one or a combination of the following: (i) a nucleic acid molecule comprising a nucleic acid sequence encoding a transposon or a fragment thereof; and (ii) a nucleic acid molecule comprising a nucleic acid sequence encoding a transposase.

17. A method for culturing isolated rat spermatogonial stem cells isolated from testis cells according to claim 1 comprising: allowing the isolated rat spermatogonial cells to adhere to a surface in a culture vessel; and culturing the isolated rat spermatogonial stem cells in culture medium according to claim 1.

* * * * *